United States Patent [19]
Goto et al.

[11] Patent Number: 5,153,563
[45] Date of Patent: Oct. 6, 1992

[54] FIRE SENSING SYSTEM, PROCESS FOR SENSING FIRE AND ENVIRONMENT MONITOR

[75] Inventors: Haruhisa Goto; Kazunari Naya; Hideo Segawa, all of Toda; Hiroomi Sato, Hachiouji; Keiichi Miyamoto, Inagi, all of Japan

[73] Assignees: Nippon Mining Co., Ltd.; Kajima Corporation, both of Tokyo, Japan

[21] Appl. No.: 569,796

[22] Filed: Aug. 21, 1990

[30] Foreign Application Priority Data

Aug. 23, 1989 [JP] Japan .................................. 1-216817
Aug. 23, 1989 [JP] Japan .................................. 1-216818
Mar. 13, 1990 [JP] Japan .................................... 2-61951

[51] Int. Cl.$^5$ .......................... G08B 17/12; F24F 7/00
[52] U.S. Cl. ..................................... 340/578; 250/339; 236/49.2
[58] Field of Search ............... 340/578, 588; 250/339; 236/49.1–49.3; 364/557

[56] References Cited

U.S. PATENT DOCUMENTS

| | | | |
|---|---|---|---|
| 4,101,767 | 7/1978 | Lennington et al. | 250/339 |
| 4,160,164 | 7/1979 | Nakauchi | 250/339 |
| 4,294,404 | 10/1981 | Gajjar | 236/49 |
| 4,463,260 | 7/1984 | Ikeda | 250/339 |
| 4,671,458 | 6/1987 | Fukuda et al. | 236/49 |
| 4,679,156 | 7/1987 | Kern et al. | 340/578 X |

FOREIGN PATENT DOCUMENTS

| | | |
|---|---|---|
| 175032 | 3/1986 | European Pat. Off. . |
| 502497 | 5/1973 | Japan . |
| 56-7196 | 1/1981 | Japan . |
| 57-96492 | 6/1982 | Japan . |

Primary Examiner—Jin F. Ng
Assistant Examiner—Thomas J. Mullen, Jr.
Attorney, Agent, or Firm—Foley & Lardner

[57] ABSTRACT

A fire sensing system, a process for sensing a fire and an environment monitor are disclosed. The system includes infrared sensors with sensing wavelength bands sensing an infrared radiation from an infrared source. One of the sensing wavelength bands is a $CO_2$-molecular resonance radiation wavelength band. The system determines whether a disastrous fire occurs or not on the basis of outputs of the sensors and a change in a ratio of the outputs. The process computes the temperature of the infrared source from a ratio of outputs of infrared sensors with at least two sensing wavelength bands of an infrared radiation from a monitored area, produces the intensity of infrared radiation of either of the bands from the computed temperature and computes a heating area from the intensity and the output of a corresponding infrared sensor. The process determines the progress of a fire. The monitor produces a control signal to an air conditioner or room heater-and-cooler from outputs of sensors and an output of a thermometer.

20 Claims, 17 Drawing Sheets

FIRE SENSING SYSTEM, PROCESS FOR SENSING FIRE AND ENVIRONMENT MONITOR

BACKGROUND OF THE INVENTION

1. Field of the Invention

The present invention relates to a fire sensing system using an infrared sensing process and more particularly to a fire sensing system separating an incident infrared radiation into a plurality of wavelength bands, sensing a change in the absolute value and the ratio of an infrared radiation of each separated wavelength band, and determining in response to the sensed time change whether a disastrous fire occurs or not. The present invention relates to a fire sensing system adapted for use in a fire prevention system used in a residence, a building, a warehouse, etc., requiring a reliable and highly sensitive fire sensing which is free from a false alarm caused by nondisastrous flaming sources such as an electric heater, a gas heater or a stove.

The present invention also relates to a technology used with an environment monitor sensing the occurrence of an indoor disastrous fire, and an indoor environment unpleasant to a person and produces a signal controlling an alarm or an air conditioner.

2. Description of the Related Art

A multitude of prior-art fire sensing methods and systems automatically sensing the occurrence of disastrous fire have been provided. These methods and systems intend to sense the occurrance of disastrous fire in a predetermined monitored area and must operate so that a malfunction due to a heating source providing no disastrous fire, e.g., a stove rarely occurs while maintaining a high sensitivity to the occurrence of a disastrous fire.

Prior-art fire sensing systems using, e.g., a phototube, bimetal or telecamera have been provided. The phototube type fire sensing system is subject to malfunction due to sunlight or light from an electric lamp, for example, because the phototube is sensitive to ultraviolet wavelengths. The bimetal type fire sensing system is insufficiently effective because of low fire-sensitivity of the bimetal. The telecamera type fire sensing system requires an excessive number of telecameras as well as a continuous monitoring by a person, so that a desired performance is difficultly obtained.

Recently, an infrared radiation sensing process for sensing an infrared radiant from a flame has been greater noticed. In this infrared radiation sensing process, both a simple system determining the occurrence of disastrous fire when it senses an infrared radiation of a predetermined level or higher and a fire sensing system (see Examined Japanese patent application publication No. SHO 56-7196) including a method of determining whether or not the level of an output signal from an infrared sensor tends to increase for a predetermined period of time or more have been proposed.

In addition, in order to increase reliability, efforts have been made in developing a technology of separately sensing two or more wavelength band of infrared radiation from a flame and of determining whether a disastrous fire occurs or not from sensed signal. One form of this technology is a system including a sensor for visible or near infrared radiation and a sensor for other infrared radiation, the system determining a nondisastrous fire when the intensity of the visible or near infrared radiation is stronger than that of the other infrared radiation such as the case of a radiation from am electric lamp, etc.

Another form of this technology is a system sensing the intrinsic spectral distribution of a flame. The spectral distribution of infrared radiation from an infrared source absent a flame, is generally in agreement with Planck's law of radiation as shown in solid lines A and C of FIG. 2 so that the higher the temperature of a heating object, the more the top of the spectral distribution shifts towards a shorter-wavelength band. On the other hand, an infrared radiant object with flame has a different intrinsic character. That is, it has a spectral distribution with a peak as shown in the solid line B of FIG. 2. The peak of the spectral distribution of the solid line B is derived from the phenomenon of $CO_2$-molecular resonance radiation at about 4.3 $\mu$m wavelength. Thus, in principle, sensing a peak of about 4.3 $\mu$m wavelength caused by $CO_2$-molecular resonance radiation senses a flame.

In order to sense the peak of about 4.3 $\mu$m wavelength, some attempts have been proposed. For example, the art of Unexamined Japanese patent application publication No. SHO 50-2497 senses the amount of radiation at the 4.3 82 m wavelength and at two wavelengths before and after the 4.3 $\mu$m wavelength and determines a presence of flame when each of the amounts of radiation at the 4.3 $\mu$m wavelength and at the two wavelengths before and after the 4.3 $\mu$m wavelength equals or exceeds a predetermined value. In addition, the art of Unexamined Japanese patent application publication No. SHO 57-96492 determines whether or not there is a depression between two projections in the amount of radiation in order to sense the occurrence of flame.

In accordance with a method of determining the occurrence of nondisastrous fire when the radiation intensity of visible or near infrared radiation is greater than the radiation intensity of the other infrared radiation as in light from an electric lamp, the occurrence of a false alarm due to a normal light from the electric lamp is rare. On the other hand, since this method determines as the occurrence of disastrous fire, the presence of a heater such as an electric heater, having no or low visible or near infrared radiation, the method produces a false alarm, so that an application of the method is very restricted.

In accordance with the method of sensing the amounts of radiation at the 4.3 $\mu$m wavelength and two wavelengths before and after the 4.3 $\mu$m wavelength and determining the presence of flame when each of the amounts of radiation at the 4.3 $\mu$m wavelength and two wavelengths before and after the 4.3 $\mu$m wavelength equals or exceeds the predetermined value, this method can sense the presence of flame but not determine whether the flame is derived from a disastrous fire or a normal or flame producing heater. That is, this method entails a drawback in that it can produce a false alarm in response to the occurrence of a flame of a gas range, gas stove or the like.

Various prior-art air conditioners sensing indoor conditions by means of a temperature sensor and a humidity sensor in order to control a room cooler and room heater or the air conditioners to thereby produce a comfortable indoor environment have been provided.

These prior-art air conditioners control an indoor temperature in response to a sensing signal from a contact type temperature sensor, e.g., a thermistor, placed in or near the body of the air conditioners. That is, the air conditioners only consider the temperature of air surrounding the temperature sensor as an average indoor temperature and controls the room heater and room cooler of the air conditioners.

The temperature which the body of an indoor person feels is the most important factor for controlling an indoor environment by means of air conditioners or room heaters and room coolers. The temperature of radiation heat which the skin of human body receives from an infrared radiant from interior surfaces of a room, contributes to the temperature which the body of the person feels in addition to the temperature of air in direct contact with the skin of the body of the person.

For example, heat radiant from a room heater, window arrangement, etc., produces a hot feeling on the human body, while a window arrangement and wall of a room that absorbs heat radiant from the human body produces the feeling of a bone-reaching chill. Thus, the prior-art method of controlling an environment in response to a single temperature output of the contact type temperature sensor such as the thermistor sensing air in contact with the sensor cannot provide a truly comfortable environment to a person.

SUMMARY OF THE INVENTION

The present invention was made in view of the above-described problems. A primary object of the present invention is to provide a fire sensing system which very rarely produces a false alarm in response to the normal conditions of heaters useful for life environment, e.g., an electric heater, a gas heater and a stove, while maintaining high-sensitivity for sensing the occurrence of disastrous fire.

Another object of the present invention is to provide a fire sensing method which also recognizes the progression of a fire.

A further object of the present invention is to provide an environment monitor which senses changes in the indoor environment inclusive of the occurrence of disastrous fire, and is able to provide an indoor environment confortable to a person, but which very rarely produces a false alarm in response to a normal condition of a useful heater, and has a high sensitivity the occurrence of disastrous fire.

The typical aspects of the present invention will be described hereinafter.

A fire sensing system of a first aspect of the present invention conprises: a plurality of band-pass filters separating an infrared radiation from an infrared source into a plurality of wavelength bands; an infrared sensor sensing infrared radiation which has passed through each of said band-pass filters, one of the wavelength bands comprising a $CO_2$-molecular resonance radiation wavelength band; and a signal processor determining whether a disastrous fire occurs or not in response to outputs of the infrared sensors and a time change in a ratio of the outputs of the infrared sensors.

The fire sensing system of the first aspect of the present invention senses $CO_2$-molecular resonance radiation when a useful flaming heater such as a gas heater and a flaming stove provides the infrared source while determining a flaming condition of a flaming heater as a nondisastrous fire since the sensed outputs of the wavelength bands and a ratio of the sensed outputs become constant. On the other hand, this fire sensing system determines as a nondisastrous fire the heating condition of a useful non-flaming heater such as an electric heater when the non-flaming heater provides the infrared source since the sensed outputs of the wavelength bands and a ratio of the sensed outputs are constant and the fire sensing system will not sense $CO_2$-molecular resonance radiation. Thus, this fire sensing system eliminates the occurrence of a malfunction caused by the normal condition of useful heater and thereby provides accurate fire sensing.

A method of a second aspect of the present invention comprises the steps of: computing the temperature of an infrared source from a ratio of outputs of a plurality of infrared sensors sensing at least two wavelength bands of infrared radiation from a monitored area; producing the intensity of infrared radiation of one of the wavelength bands from said computed temperature; and computing a heating area from the intensity of the infrared radiation and the output of an infrared sensor sensing said one of the wavelength bands, whereby the method determined the progression of a fire.

This method displays an increasing heating area on a monitor or the like, thereby providing a recognition of the progression of a disastrous fire.

An environment monitor of a third aspect of the present invention comprises: a plurality of band-pass filters separating an infrared radiant from a monitored spacing into a plurality of wavelength bands; an infrared sensor sensing an infrared radiation which has passed through each of said band-pass filters, one of the wavelength bands providing a $CO_2$-molecular resonance radiant wavelength band; and a signal processor determining the occurrence of disastrous fire and computing temperatures of the infrared radiation from the monitored spacing from outputs of the infrared sensors of the wavelength bands and from a time change in a ratio of said sensing outputs.

The environment monitor of the third aspect of the present invention measures and continuously monitors the common physical quantity of the radiation temperature in order to control the radiation temperature for environment control and on the other hand, recognizes an abnormal pattern of the radiation in the occurrence of disastrous fire and senses $CO_2$-molecular resonance radiation thereby to accurately determine whether a non-flaming electric heater, a flaming heater such as a gas heater or a flaming stove, or the occurrence of disastrous fire causes the change in the temperature of the overall environment. Thus, this environment monitor provides a comfortably controlled environment to human body and a fire-sensing free from malfunction.

The above and other objects and novel features of the present invention will be apparent from the following description, the drawings and the accompanying claims.

DESCRIPTION OF THE PREFERRED EMBODIMENTS

The present inventors studied the phenomenal difference between a disastrous fire and nondisastrous fire and concluded as follows:

The heating area and the temperature of a heater, except a disastrous fire, are fixed or become constant in a few minutes. For example, the heating area of a room heater is fixed and the temperature of the room heater becomes constant in a few minutes. In addition, the temperatures and heating areas of a match and cigarette lighter not only are essentially fixed but also extinguished in a few seconds or minutes.

Figure 3:
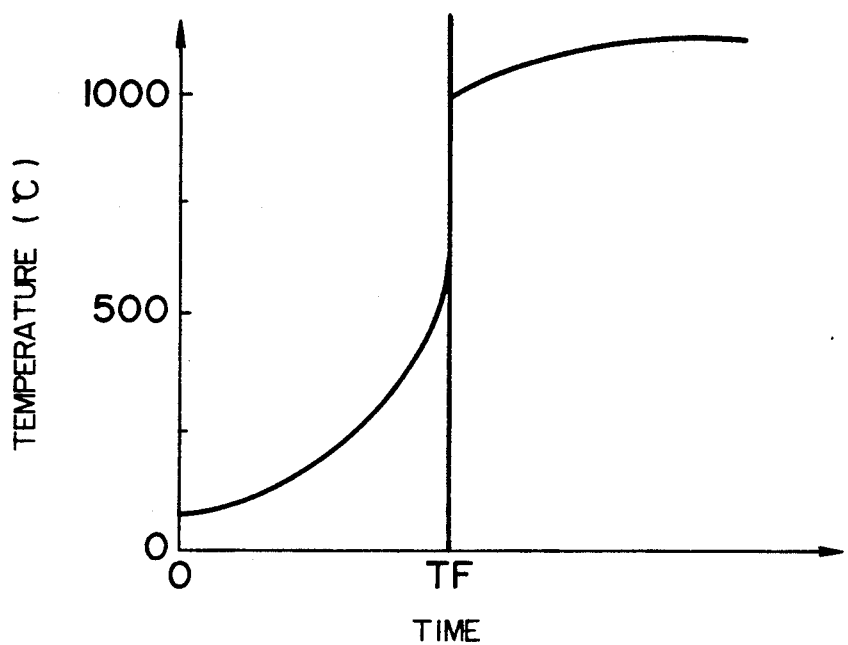
FIG. 3 is a graph representing a temperature change in the occurrence of disastrous fire.
Figure 4:
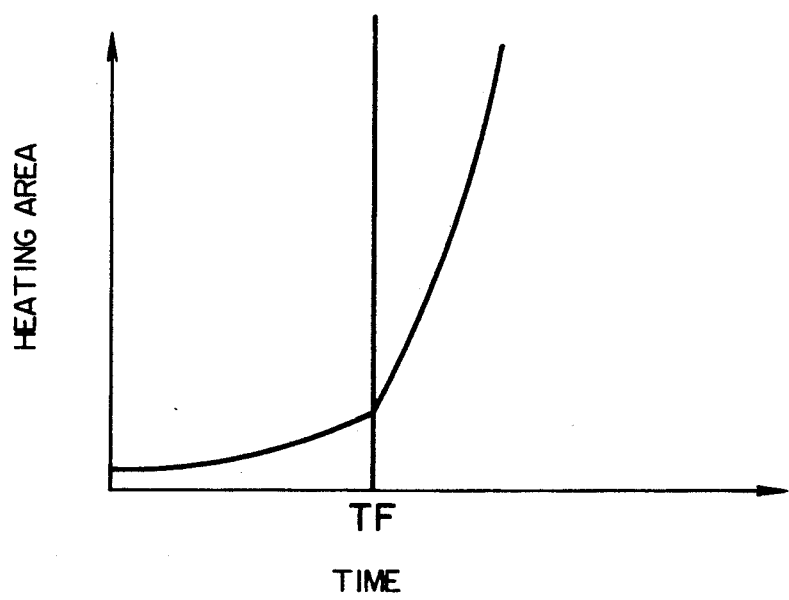
FIG. 4 is a graph representing a change in a heating area in the occurrence of disastrous fire.

On the other hand, a disastrous fire is characterized in that both the heating area and the temperature of the disastrous fire concurrently increase at the outbreak of the disastrous fire and also tend to continue to increase for a few minutes even after the outbreak of the disastrous fire. FIG. 3 represents a temperature change in a progression from a smoking condition to a disastrous fire. FIG. 4 represents a change in heating area in the progression from the smoking condition to the disastrous fire. In FIGS. 3 and 4 TF represents a flaming point of time. On the other hand, a disastrous fire without a progression from a smoking condition, e.g., an incendiary fire, produce a temperature change after the TF point of time of FIG. 3 and a change in heating area after the TF point of time of FIG. 4.

In a disastrous fire, when the infrared radiation from the fire is separated into a plurality of wavelength bands between a short-wavelength band and long-wavelength band, sensing outputs of the wavelength bands increase with time and a time change in ratios of the sensing outputs has a characteristic behavior. That is, the intensity of each sensing output reflects the area and temperature of a heater and on the other hand, since a ratio of the sensing outputs reflects the temperature of the heater, the sensing outputs of the wavelength bands and the ratio of the sensing outputs tend to concurrently increase in the case of a smoking disastrous fire and then rapidly increase when the smoking fire transfers to a flaming fire. Then, the heating area of the heater still increases while an increase in the temperature of the heater tends to level off so that the sensing outputs of the wavelength bands increase while, the ratio of the sensing outputs essentially becomes constant. Then, at the point of time when the disastrous fire has transferred to a flaming fire, $CO_2$-resonance radiation is significantly increased so that the intensity of the $CO_2$-molecular resonance radiation is increased with an increase in a firing area. On the other hand, a flame which has become constant i.e., that not of a disastrous fire, does not produce such a time change.

The inventors also took the occurence of disastrous fire as an environmental change and studied a technology of monitoring the environment of a residential spacing and a fire-sensing technology from the same viewpoint. This study has concluded that in order to produce an environment which a person staying in a room feels most comfortable, the best environment control method monitors not only the air temperature of the interior of the room but also the radiation temperature of the interior of the room. The inventors have conceived that since an infrared sensor can be used to monitor radiation temperature as well as for a method of sensing a disastrous fire by means of a radiation temperature, a single infrared sensor can produce an output for controlling indoor environment by means of the air conditioner or the like and for fire-sensing.

Then, the inventors studied in more detail an environment control and a fire-sensing performed in response to the radiation temperature. Thus, the inventors discovered that the indoor radiation temperature was computed from the ratios of outputs from a plurality of infrared sensors and in addition, providing a contact type temperature sensor such as a thermistor, monitor the temperature which a human body staying in a sensed spacing actually feels, in order to control an environment so that the human body feels comfortable.

Since the temperature of an indoor environment is usually about 300 K. (i.e., 23° C.), the top of a radiation wavelength is about 10 μm. Thus, the infrared sensor preferably has a band-pass filter with a 10 μm central pass wavelength.

On the other hand, when a monitored environment includes an non-flaming room heater such as an electric heater, monitoring the environment by means of a single infrared sensor with the 10 μm band-pass filter determines that the temperature of the overall environment increases even when the electric heater increases the temperature of part of the environment. Thus, a monitoring of the environment by means of an infrared sensor with a band-pass filter with an about 4 μm central pass wavelength may be preferably added.

Since the intensity of a 4 μm wavelength infrared radiation from an environment without room heater is sufficiently lower than that of a 10 μm wavelength infrared radiation of the infrared radiation from the environment without room heater and, the intensities of 4 μm and 10 μm wavelength infrared radiations of an infrared radiation from an environment with a non-flaming room heater such as an electric heater are essentially equal, both increases in the intensities of the 4 μm and 10 μm wavelength infrared radiations of the latter case provide a determination that the non-flaming room heater heats up and on the other hand, a low intensity of the 4 μm wavelength infrared radiation of the latter case provides a determination that the temperature of the overall environment increases.

Thus, the following embodiments of the present invention provide a fire-sensing system producing essentially no false alarms (i.e., very rarely producing a false alarm) in response to a normal operation of a useful heater in a living environment, high sensitivity for sensing a disastrous fire, a fire-sensing method recognizing a progression of a fire in addition to the operations of the above fire-sensing system, and an environment monitor providing an indoor environment which is comfortable to a person.

FIRST EMBODIMENT

Figure 1:
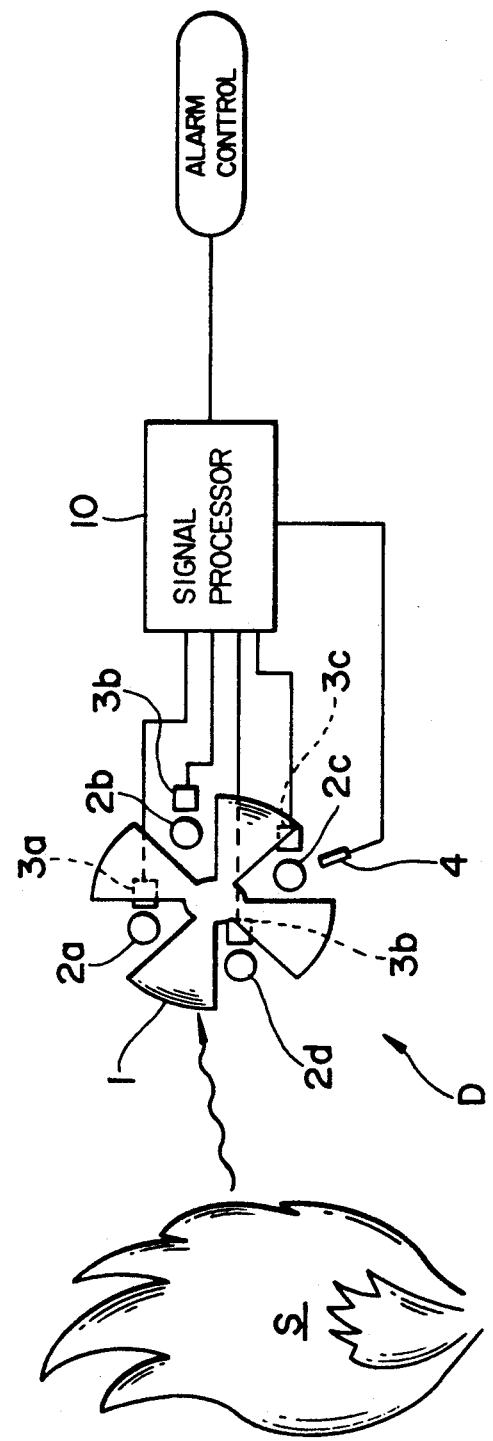
FIG. 1 is a schematic diagram of the fundamental arrangement of a fire-sensing system of one embodiment of a first aspect of the present invention.

FIG. 1 is a schematic diagram of the fundamental arrangement of a fire-sensing system of one embodiment of the first aspect of the present invention;

An infrared radiation sensing unit D receives infrared radiation from an infrared source S to separate the infrared radiation into a plurality of wavelength bands and to sense the intensity of each of the wavelength bands.

The infrared radiation sensing unit D comprises: a rotational chopper 1 periodically chopping the infrared radiation from the infrared source S; four band-pass filters $2a$, $2b$, $2c$ and $2d$ each of which comprises an optical filter with a different pass band, which is not restricted to a particular form; and four infrared sensors $3a$, $3b$, $3c$ and $3d$ each sensing passing infrared radiation through the corresponding band-pass filters $2a$ to $2d$. In accordance with the four-split system of the first embodiment of the present invention, the central wavelengths of the pass bands of the band-pass filters $2a$ to $2d$ are suitably selected so that, e.g., the pass-band central wavelength of the band-pass filter $2a$ is 2-3 μm, that of the band-pass filter $2b$ is 3-4 μm, that of the band-pass filter $2c$ is 4-5.5 μm and that of the band-pass filter $2d$ is 8-15 μm and so that the pass-band of each of the band-pass filters $2a$ to $2d$ is 0.1-1.5 μm. One of the band-pass filters $2a$ to $2d$ allows the wavelength band (i.e., 4.3 μm) of $CO_2$-molecular resonance radiation to pass. In the first embodiment, the band-pass filter $2c$ allows $CO_2$-molecular resonance radiation to pass. It should be avoided that the pass-band central wavelength of one of the band-pass filters $2a$ to $2d$ is 5.5-8 μm, since steam contained in the air absorbs a very great amount of a 5.5-8 μm wavelength infrared radiation. The number of split pass-bands will not be restricted to four but may be two or more. This number is sufficiently practically up to at least 5.

An optical filter for the band-pass filters $2a$ to $2d$ comprises a multilayer film in which, one of ZnSe, ZnS, Ge and other dielectrics are alternatively vacuum deposited one another on a substrate made of Si or the like. The thickness of the multilayer film is determined in accordance with a target pass-band.

The infrared sensors $3a$ to $3d$ may be a semiconductor infrared sensor, a thermopile or a pyroelectric infrared sensor. The semiconductor infrared sensor is less preferable since it requires cooling. The thermopile or pyroelectric infrared sensor is preferable. The pyroelectric infrared sensor is most preferable. When each of the infrared sensors $3a$ to $3d$ is made with a thermopile, the chopper 1 may be alternatively eliminated. Since the pyroelectric infrared sensor is a differentiation sensor operating in response to only a temperature differential, it is optimum for the inventive system sensing a temperature increase. The pyroelectric infrared sensor has an arrangement in which the top surface and back surface of a thin plate made of a pyroelectric material such as lithium tantalate or $Pb_xZr_yO_3$ have electrodes deposited thereon by vacuum deposition etc. A Si-photodiode may be alternatively used in order to sense a near-infrared band with a wavelength of an about 1 μm.

A pulse motor and a direct current motor (i.e., DC motor) suitably rotates the chopper 1. The DC motor requires a rotational speed sensor such as a photointerrupter 4 in order to sense a rotational speed of the chopper 1. The pulse motor requires no interrupter since a driving pulse signal for the pulse motor provides a rotational speed of the pulse motor.

A signal processor 10 receives and processes outputs of the infrared sensors $3a$ to $3d$ and a rotational speed sensing signal of the chopper 1 from the photointerrupter 4.

The signal processor 10 operates the magnitudes of the outputs of the infrared sensors $3a$ to $3d$, ratios of the outputs and time changes in the magnitudes of the outputs and the ratios of the outputs, determines whether the monitored infrared source S is a disastrous fire or not on the basis of the results of the operation, and producing a signal for driving an alarm when monitored infrared source S is determined to be a disastrous fire.

Figure 5:
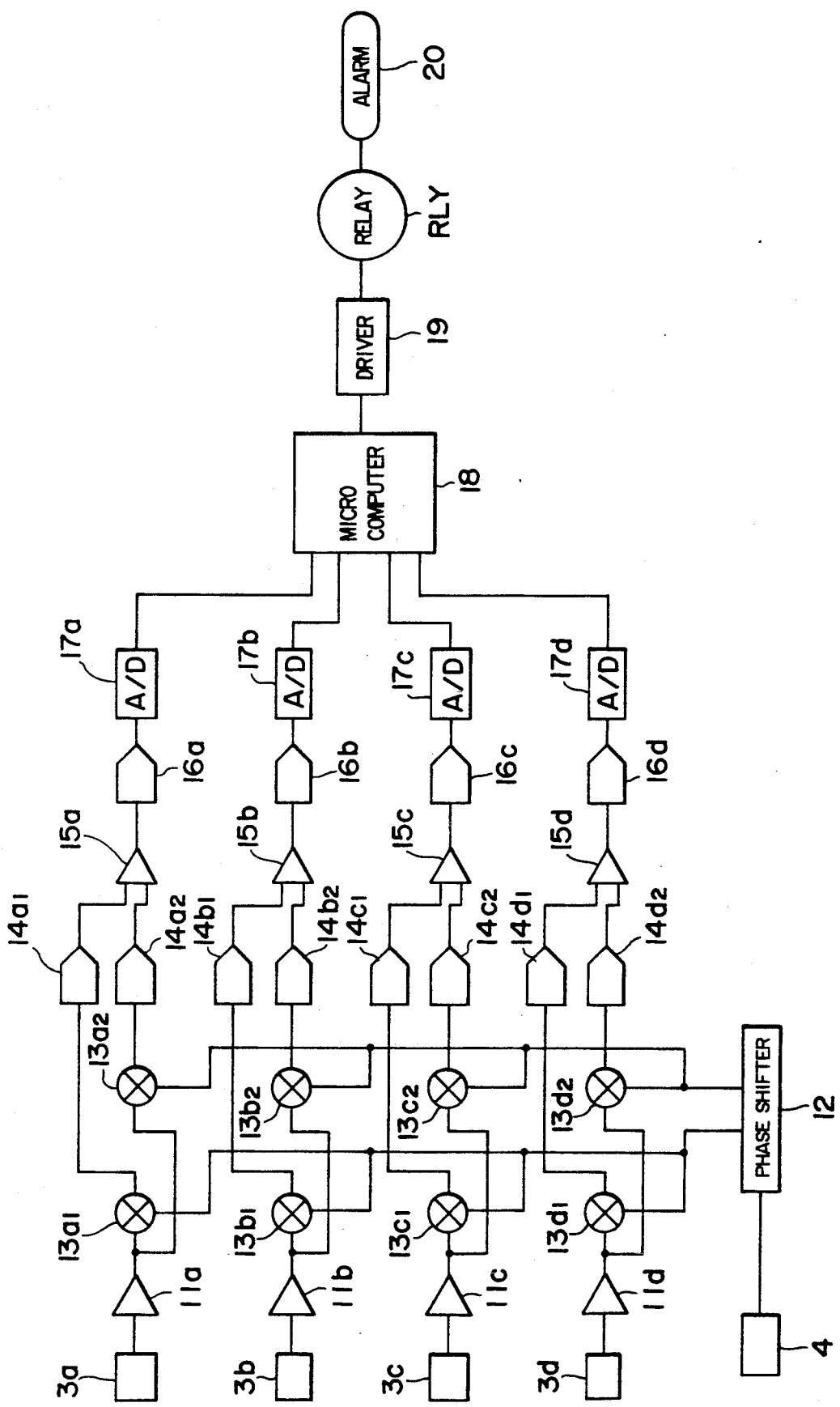
FIG. 5 is a circuit block diagram of one embodiment of a signal processor.

FIG. 5 represents one example of the signal processor 10. Amplifiers $11a$, $11b$, $11c$ and $11d$ receive outputs of the infrared sensors $3a$ to $3d$ and amplify them to desired levels. A phase shifter 12 receives the rotational speed sensing signal from the photointerrupter 4 and produces synchronizing signals SIN $\phi$ and COS $\phi$, 90 degrees phase-shifting from each other.

Synchronous detectors $13a_1$, $13b_1$, $13c_1$, and $13d_1$, and $13a_2$, $13b_2$, $13c_2$ and $13d_2$ receive and detect the outputs of the amplifiers $11a$ to $11d$ in synchronization with the synchronizing signals SIN $\phi$ and cos $\phi$. Square multipliers $14a_1$, $14b_1$, $14c_1$, and $14d_1$, and $14a_2$, $14b_2$, $14c_2$ and $14d_2$ square the detection outputs of the synchronous detectors $13a_1$ to $13d_1$ and $13a_2$ to $13d_2$. Adders 15a, 15b, 15c and 15d add outputs of the square multipliers $14a_1$ to $14d_1$ and $14a_2$ to $14d_2$ for each channel. Square root processors 16a, 16b, 16c and 16d square root the outputs of the respective adders 15a to 15d. Thus, an operation of respectively synchronization-sensing 90-degree phase-shifting synchronizing signals of each pair and then producing an average of squared synchronization detecting outputs eliminates a phase deviation caused by misalignment, etc. between chopper 1 and each of the infrared sensors 3a to 3d. A/D converters 17a to 17d A/D convert the outputs of the square root processors 16a to 16d. A microcomputer 18 receives and processes the outputs of the A/D converters 17a to 17d. In the FIG. 5 embodiment, analog square multipliers produce means squares. Alternatively, A/D converting the synchronization-detected signals and applying them to a microcomputer can provide a mean square of them. Alternatively, A/D converting the outputs of the amplifiers 11a to 11d allows the microcomputer 18 to synchronization detect them.

The microcomputer 18 operates on the sensing signals at intervals of a few seconds by timer interruption, stores data of an increase in the temperature of the infrared source and an increase in a heating area and of the presence or absence of $CO_2$-molecular resonance radiation, monitors on the data to see whether the temperature and heating area of the infrared source continuously increase or not, determines an occurrence of a disastrous fire when the temperature and heating area of the infrared source are increasing, and operates a driver 19 to turn a relay RLY on, thereby to operate an alarm 20.

Figure 6:
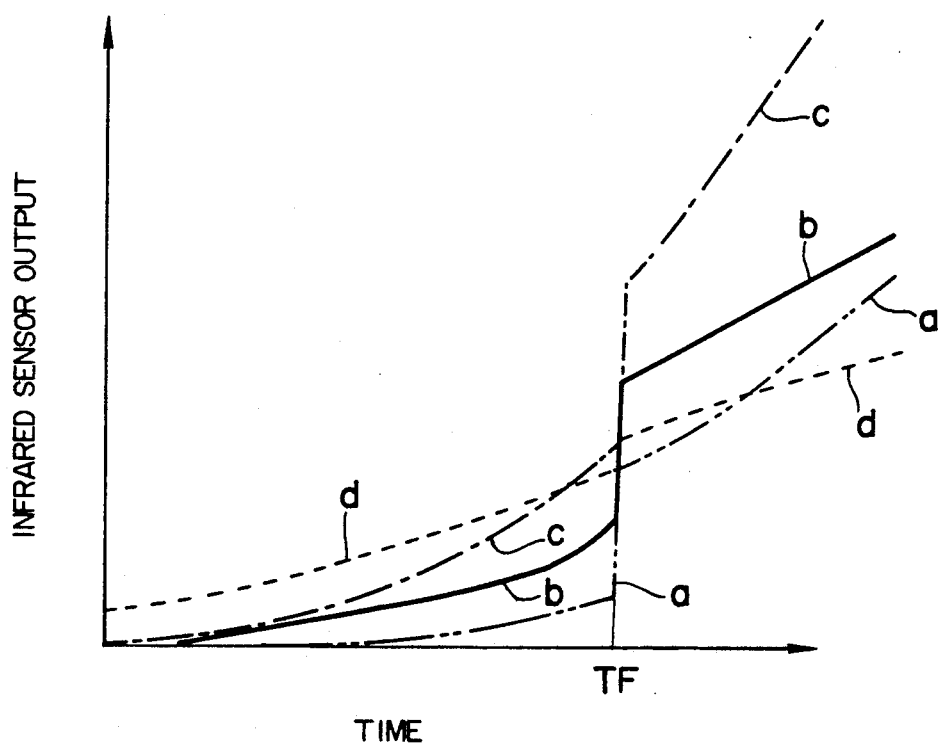
FIG. 6 is a graph representing a change in the output of each infrared sensor of the fire-sensing system of FIG. 1 in the occurrence of disastrous fire.

In particular, the outputs of the infrared sensors 3a to 3d change in the case of a disastrous smoking fire as shown in FIG. 6. That is, the outputs a, b, c and d of the infrared sensors 3a to 3d increase with a temperature increase and an increase in a fire-spreading area in the sequence of the outputs d, c, b and a. Since $CO_2$-molecular resonance radiation sharply rises at the flaming point of time TF, the output c of the infrared sensor 3c of the outputs of the infrared sensors 3a to 3d sharply rises. Then, since the infrared source flames after the flaming point of time TF, the temperature increase is low and an increase in the amount of infrared radiation caused by an increase in the fire spreading area becomes predominate, so that the outputs a, b, c and d of the infrared sensors 3a to 3d increase but the ratios of the outputs a, b, c and d essentially becomes constant.

Thus, a comparing outputs of the infrared sensors 3a to 3d provides a temperature of the infrared source and in particular comparing, e.g., the outputs of the infrared sensors 3a, 3b and 3d of the infrared sensors 3a to 3d at the temperature of the infrared source with predetermined values provides a heating area. In addition, computing from the temperature and heating area of the infrared source produced in the above sequence of operation a blackbody radiation intensity of the infrared source, i.e., an infrared radiation intensity of the $CO_2$-molecular resonance radiation wavelength band if the infrared source is a blackbody and comparing the resulting value of the blackbody radiation intensity with the output of the infrared sensor 3c sensing a $CO_2$-molecular resonance radiation band provide the presence or absence of $CO_2$-molecular resonance radiation.

Thus, when the temperature and heating area of the infrared source tend to increase for a fixed period (i.e., a few minutes) but no $CO_2$-molecular resonance radiation is recognized, the occurrence of a disastrous smoking fire is determined. When, the temperature and heating area of the infrared source sharply rise at a point of time and $CO_2$-molecular resonance radiation is concurrently recognized, the microcomputer 18 determines that the disastrous smoking fire has transferred to a disastrous flaming fire and increases the sound volume of the alarm 20 or changes the intensity of the sound of the alarm so as to alarm the transference. When a case in which no infrared radiation is sensed suddenly passes into a case in which $CO_2$-molecular resonance radiation is sensed, a heating at a high temperature corresponding to $CO_2$-molecular resonance radiation is sensed and the heating area sharply rises, the microcomputer 18 determines the case as an occurrence of incendiary fire. On the other hand, when no increase in a heating area is recognized, the microcomputer 18 determines the case as a presence of a flaming heater, e.g., a flaming stove.

Thus, the present invention determines the presence or absence of disastrous fire on the basis of actual fire phenomenon, thereby greatly reducing the number of occurrences of a false alarm as compared to prior art fire sensing systems.

Figure 7:
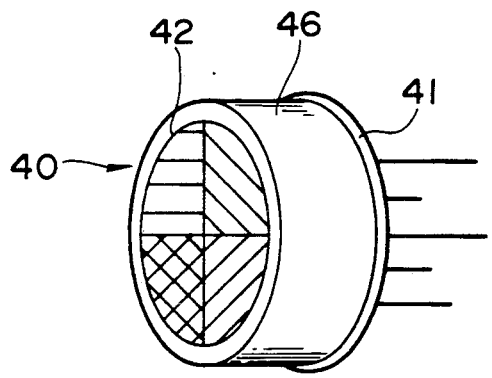
FIG. 7 is a perspective view of one example of a package type infrared sensor.
Figure 8:
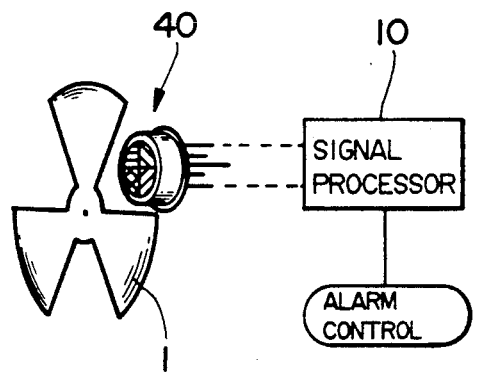
FIG. 8 is an illustration of a fire-sensing system with the package type infrared sensor of FIG. 7.
Figure 9:
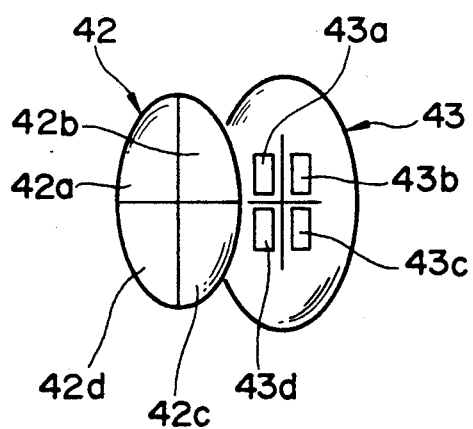
FIG. 9 is an exploded perspective view of the package type infrared sensor of FIG. 7, representing the interior thereof.
Figure 10:
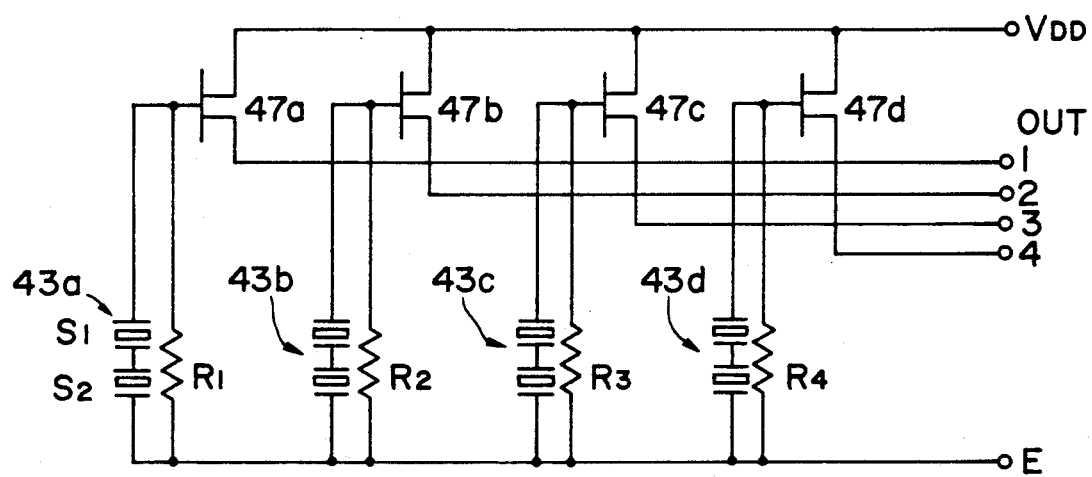
FIG. 10 is a circuit diagram of one example of a circuit of the package type infrared sensor of FIG. 7.

FIGS. 7-9 illustrate an arrangement and a use of a pyroelectric sensing unit 40 packaging four band-pass filters 42a, 42b, 42c and 42d and four pyroelectric infrared sensors 43a, 43b, 43c and 43d. FIG. 10 illustrates a circuit of the pyroelectric sensing unit 40. In FIGS. 7-10, the four pyroelectric infrared sensors 43a to 43d together form a single unit unlike the above-described embodiment of the present invention with the four infrared sensors separate from each other. As shown in FIG. 9, the infrared sensing unit 40 comprises: four pyroelectric sensors 43a, 43b, 43c and 43d separately mounted within four quadrants of a disc-shaped insulating substrate 41; a window 42 of four-split band-pass filters 42a, 42b, 42c and 42d each provided in front of corresponding one of the respective pyroelectric materials; and a sealing can 46 connecting the insulating substrate 41 to the window 42, the infrared radiation sensing unit 40 providing a packaged sensor sensing the four wavelength bands of infrared radiation. The central pass-band wavelengths of the four band-pass filters 42a to 42d are 2.6 $\mu$m, 3.7 $\mu$m, 4.3 $\mu$m and 9 $\mu$m. The pass-band of each of the band-pass filters 42a to 42d is 0.1-1 $\mu$m. The four-split band-pass filter assembly of the band-pass filters 42a to 42d is made with four dielectric multilayer films each selectively deposited on a single transparent glass substrate or four segment-type band-pass filters attached to a single transparent glass. The pyroelectric infrared sensors 43a to 43d sense the respective wavelength bands of infrared radiation passing through the band-pass filters 42a to 42d. The signal processor 10 processes the resulting sensing outputs of the pyroelectric infrared sensors 43a to 43d as in the above-described embodiment. The sealing can 46 preferably contains partition walls separating the interior spacing of the sealing can 46 into four sections.

As shown in FIG. 10, each of the pyroelectric infrared sensors 43a to 43d comprises a pair of pyroelectric elements $S_1$ and $S_2$ oppositely polarized and serially connected, one terminal of pyroelectric elements $S_1$ of the pyroelectric infrared sensors 43a to 43d being connected to a gate terminal of the corresponding one of impedance transposition FETs 47a, 47b, 47c and 47d. A drain terminal of each of the impedance transposition FETs 47a to 47d receives the positive voltage $V_{DD}$ of an electric power source. A source terminal of each of the impedance transposition FETs 47a to 47d produce an output signal. A terminal of the other pyroelectric infrared sensing element S2 is connected to ground E. Respective input resistors $R_1$, $R_2$, $R_3$ and $R_4$ are connected between the gate terminals of the impedance transposition FETs 47a to 47d and ground E.

The respective impedance transposition FETs 47a to 47d are mounted near the pyroelectric infrared sensors 43a to 43d. The input resistors $R_1$ to $R_4$ are mounted on the insulating substrate 41. Each of the impedance transposition FETs 47a to 47d is connected to the corresponding one of the infrared sensors 43a to 43d and input resistors $R_1$ to $R_4$ by means of a bonding wire or soldering. The connected impedance transposition FETs 47a to 47d, pyroelectric infrared sensors 43a to 43d and input resistors $R_1$ to $R_4$ are sealed within the sealing can 46.

SECOND EMBODIMENT

A fire-sensing system embodying a fire-sensing method of the second aspect of the present invention is essentially the same as the fire-sensing system of FIG. 1.

Figure 11:
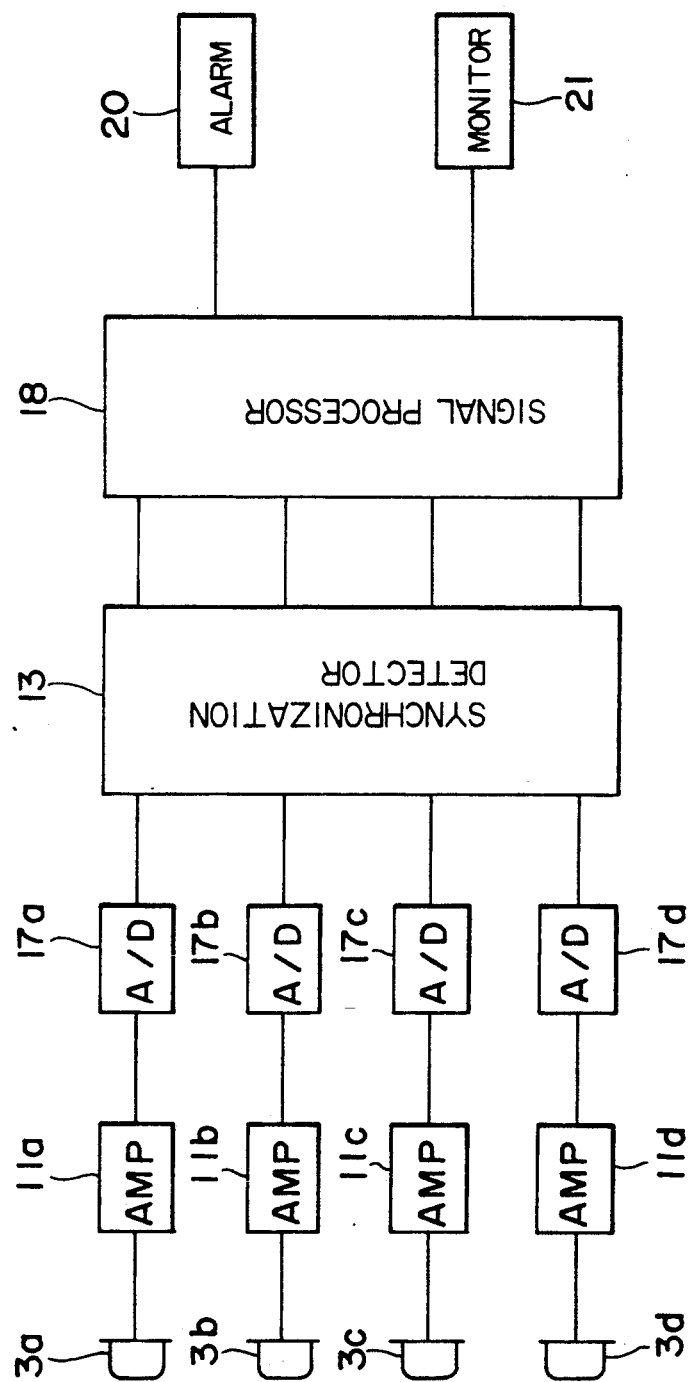
FIG. 11 is a circuit block diagram of one embodiment of a signal processor of a fire-sensing system of a second aspect of the present invention.

FIG. 11 represents an example of a signal processor 10 of the second embodiment of the present invention. Amplifiers 11a, 11b, 11c and 11d receive outputs of the infrared sensors 3a to 3d and amplify them to desired levels.

A/D converters 17a to 17d A/D convert the amplified sensing outputs of the amplifiers 11a to 11d and feed them to the synchronous detector 13. A signal processor 18 comprising a microcomputer or the like, receives detection outputs of the synchronous detector 13 and produces a mean square of two detection outputs at a 90 degree phase-shifting from each other to eliminate a phase shift caused by a spatial displacement between a chopper and infrared sensors, etc.

The microcomputer 18 operates on the synchronous detection outputs at intervals of a few seconds by timer interruption, stores data of a temperature increase of the infrared source and an increase in heating area and of the presence or absence of $CO_2$-molecular resonance radiation, monitors on the data whether the temperature and heating area of the infrared source continuously increase or not, determines the occurrence of a disastrous fire when the temperature and heating area of the infrared source are increasing, operates an alarm 20 and displays an increase in a computed heating area on a monitor 21.

In accordance with the second embodiment, the synchronization detector 13 and signal processor 18 are separate. However, a single microcomputer may alternatively replace the synchronous detector 13 and signal processor 18.

Computing the temperature and heating area of the infrared source by means of the signal processor 18 will be described hereinafter.

Where the intensities per unit area of a surface for receiving infrared radiations falling on the infrared sensors 3a to 3d are Pa, Pb, Pc and Pd and outputs of the synchronous detectors 13a to 13d are Va, Vb, Vc and Vd, the outputs Va to Vd are represented as follows:

Va = Pa × Aa,
Vb = Pb × Ab,
Vc = Pc × Ac, and
Vd = Pd × Ad, wherein Aa to Ad are constants determined by the properties of the infrared sensors, band-pass filters and amplifiers. In Plank's law of radiation, the blackbody radiation intensity per unit area of an infrared radiation at λ-wavelength from an object at a temperature T is represented by the following equation:

$$P(\lambda, T) = \frac{C_1}{\lambda^5} \times \frac{1}{\exp\frac{C_2}{\lambda T} - 1} \quad (1)$$

wherein $C_1$ and $C_2$ are constants determined by the equations $C_1 = 2hc^2$ and $C_2 = hc/k$, h: Planck constant; C: light velocity; k: Boltzmann constant.

Substituting $\lambda_1$ and $\lambda_2$ wavelength bands of two infrared sensors and the infrared intensities $P_1$ and $P_2$ of the sensed bands into the equation (1) derives the following approximate equation (2) producing the temperature T:

$$T \approx C_2 \times \frac{\lambda_1 - \lambda_2}{\lambda_1 \lambda_2} \times \frac{1}{\ln \frac{P_2}{P_1} \times \frac{\lambda_2^5}{\lambda_1}} \quad (2)$$

Substituting the sensing outputs Va and Vd of the infrared sensors 3a and 3d for λa and λd wavelength bands into the infrared intensities $P_1$ and $P_2$ of the $\lambda_1$ and $\lambda_2$ wavelength bands derives the following equation (3) from the equation (2):

$$T = C' \times \frac{\lambda_a - \lambda_d}{\lambda_a \lambda_d} \times \frac{1}{\ln \frac{Vd}{Va} \times \frac{\lambda_d^5}{\lambda_a}} \quad (3)$$

wherein C' is a constant in which constant $C_2$ is operated by constants Aa and Ad of detection outputs of the wavelength bands.

The equation (3) shows that providing two infrared sensors with two different sensing wavelength bands produces the temperature T of a disastrous fire or heater from a ratio of two sensing outputs of the infrared sensors.

Thus, the temperature T produced by the equation (3) provides the blackbody radiation intensity Pa' at λa-wavelength per unit area in accordance with Planck's law of radiation, i.e., the equation (1).

On the other hand, since the air disperses and absorbs an infrared radiation from the heater the incident intensity of the infrared radiation to the infrared sensor fails to equal the intensity of the infrared radiation from the heater and the incident intensity of the infrared radiation is in inverse proportion to a distance between the infrared sensor and the heater. Since Pa' represents the blackbody radiation intensity per unit area of the heater, the incident intensity of the infrared radiation is considered to be in proportion to the area of the surface of the heater. An experience of the present inventors taught that the sensing output Va' at λa wavelength of a sensing system could be estimated by the following equation (4):

$$Va' = \frac{Pa' \times S}{2\pi l^2} \times Aa \quad (4)$$

and the computed sensing output Va' approximately equalled an actual sensing output Va. In the equation (4), S represents the area of the surface of the heater, Aa represents a constant at a λa-wavelength determined by the properties of the infrared sensors, band-pass filters and amplifiers, and l represents a distance between the infrared sensor and the heater. Thus, the area S of the surface of the heater is computed by the following equation (5):

$$S = \frac{2\pi l^2 \times Va}{Pa' \times Aa} \quad (5)$$

The second embodiment computed a heating area by means of the equation (5) thereby to recognize a progression of a disastrous fire.

The above-description with the equations 1-5 have provided a method of obtaining the temperature T and area S of the heater from the sensing outputs of the infrared sensors $3a$ and $3d$. The sensing outputs of the infrared sensors $3a$ and $3c$ or the sensing outputs of the infrared sensors $3c$ and $3d$ may alternatively provide the temperature T and the area S of the surface of the heater.

In addition, an experience of the present inventors taught that changing an infrared sensor used in computation in response to the temperature T of the heater provided a more accurate temperature T and a more accurate area S.

Figure 12:
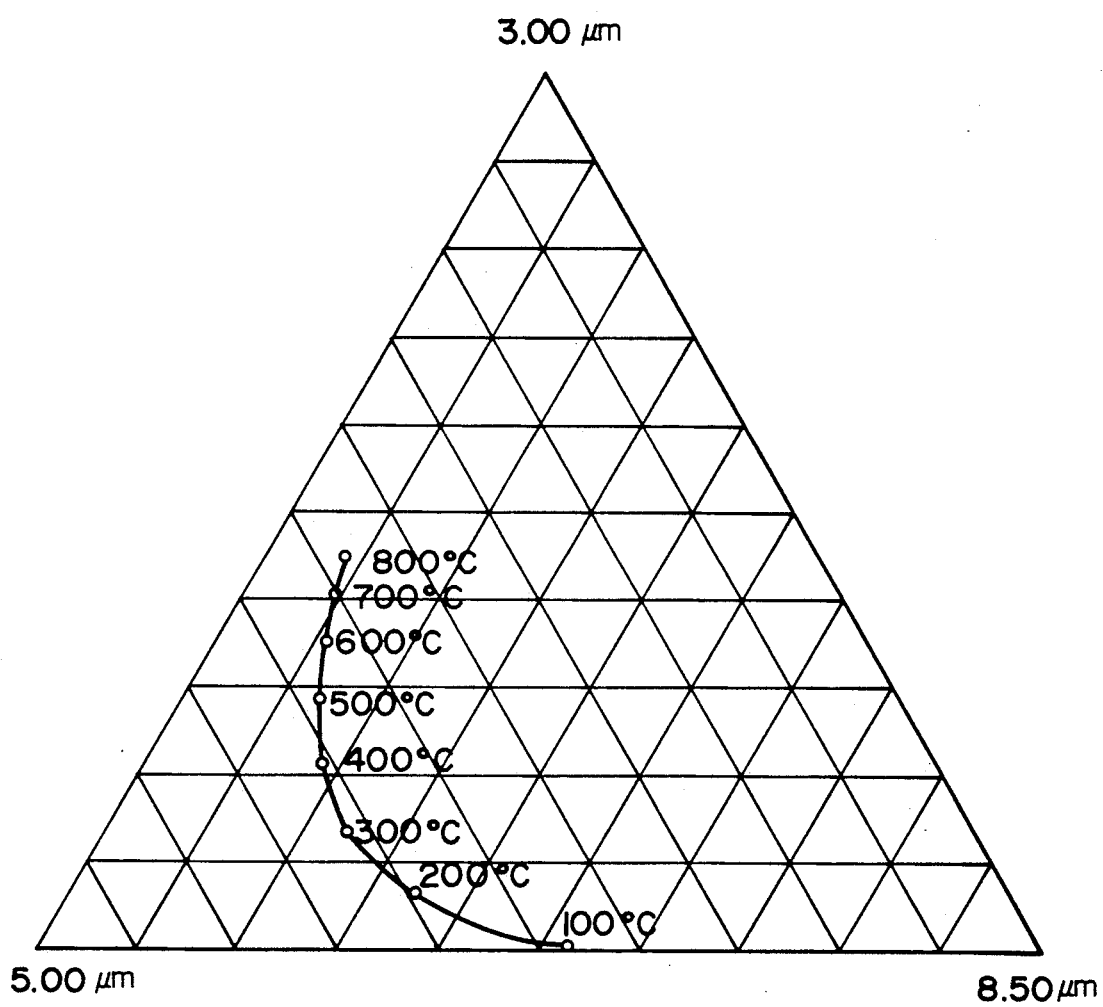
FIG. 12 is a graph representing ratios of sensing outputs of infrared sensors of a fire-sensing system of the second aspect of the present invention.

FIG. 12 represents ratios of sensing outputs of the infrared sensors $3a$, $3c$, and $3d$ of the FIG. 11 embodiment when the central wavelength $\lambda a$ of the infrared sensor $3a$ is 3 $\mu m$, the central wavelength $\lambda c$ of the infrared sensor $3a$ is 5 $\mu m$, and the central wavelength $\lambda d$ of the infrared sensor $3d$ is 8.5 $\mu m$. FIG. 12 represents that the more approximate to each apex each of the central wavelengths is, the greater the ratios of the sensing outputs of the infrared sensors. As seen in FIG. 12, when the temperature of a heater is 300°-400° C., the temperature dependency of the ratio of the sensing outputs of the infrared sensors $3c$ and $3d$ with the central wavelengths $\lambda c$ and $\lambda d$ is great and, when the temperature of a heater is 400° C. or more, the temperature dependency of the ratio, of the sensing outputs of the infrared sensors $3a$ and $3c$ with the central wavelengths $\lambda a$ and $\lambda c$ is great. That is, when the heater at a temperature relatively as low as 300°-400° C. is sensed, a combination of the infrared sensors $3a$ and $3d$ is good and when, the heater at a temperature as high as 400° C. or more is sensed, a combination of the infrared sensors $3a$ and $3c$ provides a good measurement accuracy. Thus, providing three temperature-measuring bands provides an accurate temperature and an accurate area of the heater over the range of low temperature to high temperature.

Figure 2:
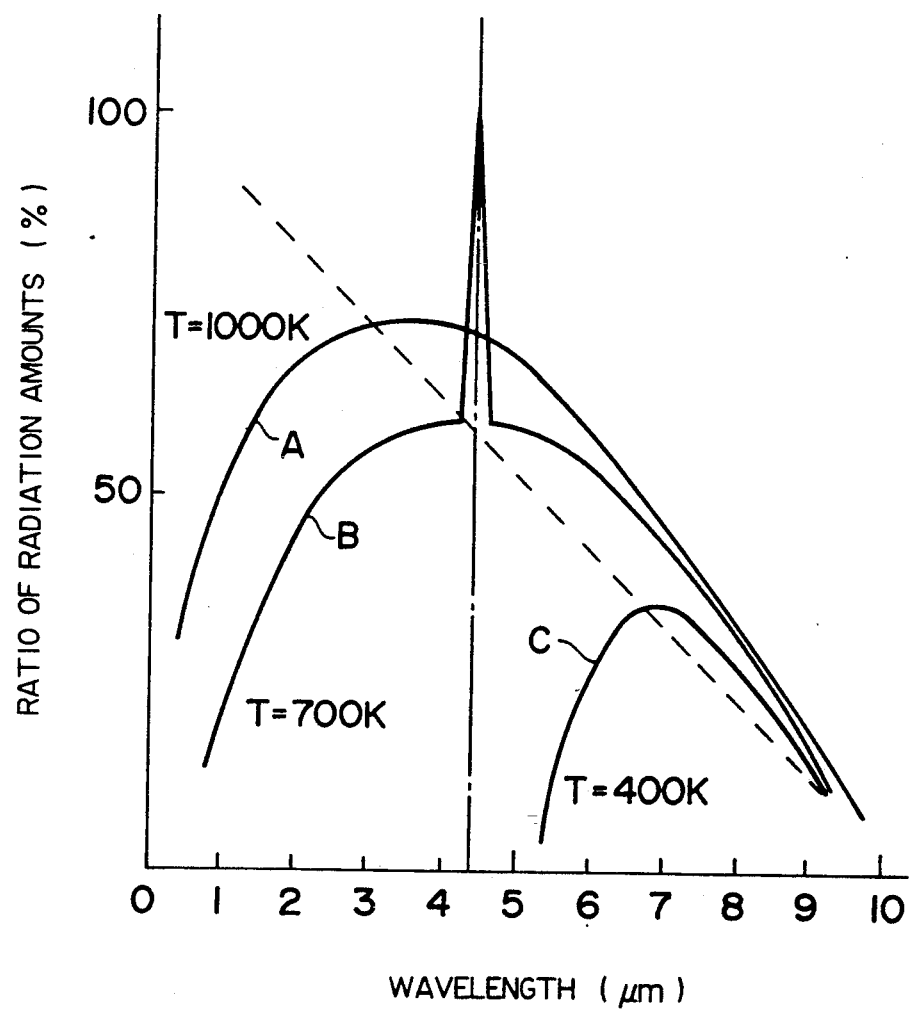
FIG. 2 is a graph representing a relationship between the wavelength and amount (relative value) of an infrared radiation from an infrared source.

In accordance with the above-described computations of the temperature and heating area of the heater performed by the signal processor 18 of the second embodiment, computing the temperature T and heating area S of the heater and substituting the temperature T and the wavelength $\lambda_{CO2}$ of a $CO_2$-molecular resonance radiation band into the equation (1) representing Planck's law of radiation, produces the radiation intensity $P_{CO2}$ of the $CO_2$-molecular resonance radiation band, and substituting the radiation intensity $P_{CO2}$ and the heating area S computed by the equation (5) into the equation (4) estimates a sensing output Vb' of an infrared sensor at the $CO_2$-molecular radiation band. When the heater is assumed a blackbody, the sensing output Vb' has its real value. Thus, when the heater flames, a peak appears at the $CO_2$-molecular resonance radiation band as shown in FIG. 2. Thus, comparing the estimated sensing output Vb' with an actual sensing output Vb of the infrared sensor $3b$ determines that the heater flames, when the actual sensing output Vb exceeds the estimated sensing output Vb'.

EXAMPLE OF THE SECOND EMBODIMENT

An experimental apparatus including three infrared sensors with 3.629 $\mu m$, 4.736 $\mu m$ and 12.048 $\mu m$ central sensed wavelengths was provided so that the infrared sensors were placed at 2.4 m above a floor. A 16 cm × 16 cm heating panel, methanol contained a vessel with a 10 cm × 10 cm square top opening and 10 of 18 cm × 18 cm news papers provided on the same heating panel were prepared in order to conduct a test of flaming the methanol and setting a fire on the news papers. The monitoring area of each of the infrared sensors was a circle with a 7-m diameter.

Figure 13:
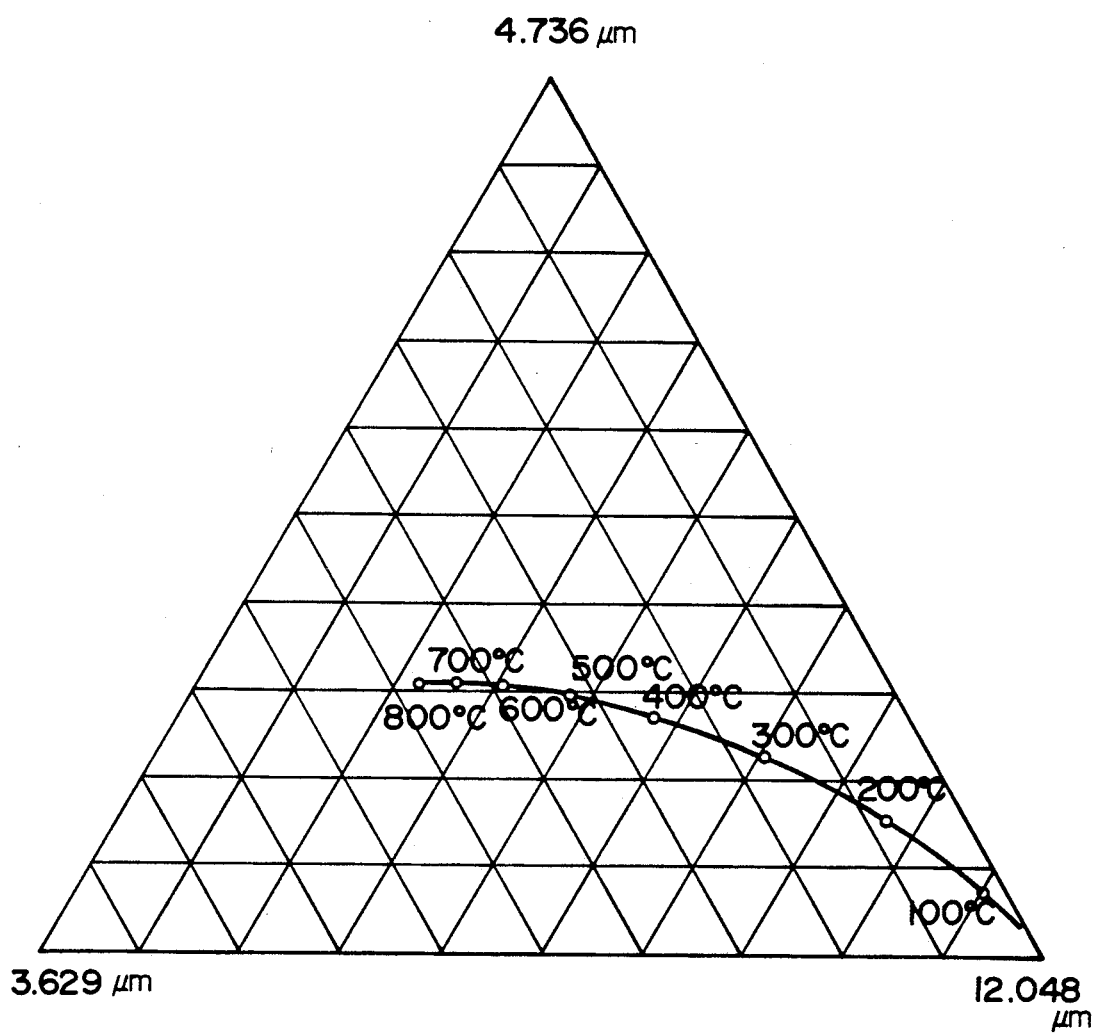
FIG. 13 is a graph representing ratios of the theoretical values of sensing outputs of the infrared sensors of an experimental system of the second aspect of the present invention.

FIG. 13 represents the ratios of theoretical sensing outputs of the infrared sensors of the experimental apparatus computed by the equations (1) and (4) for each range of 100° C. within 100°-800° C. so that the surface area of a heater is assumed 256 cm².

Figure 14:
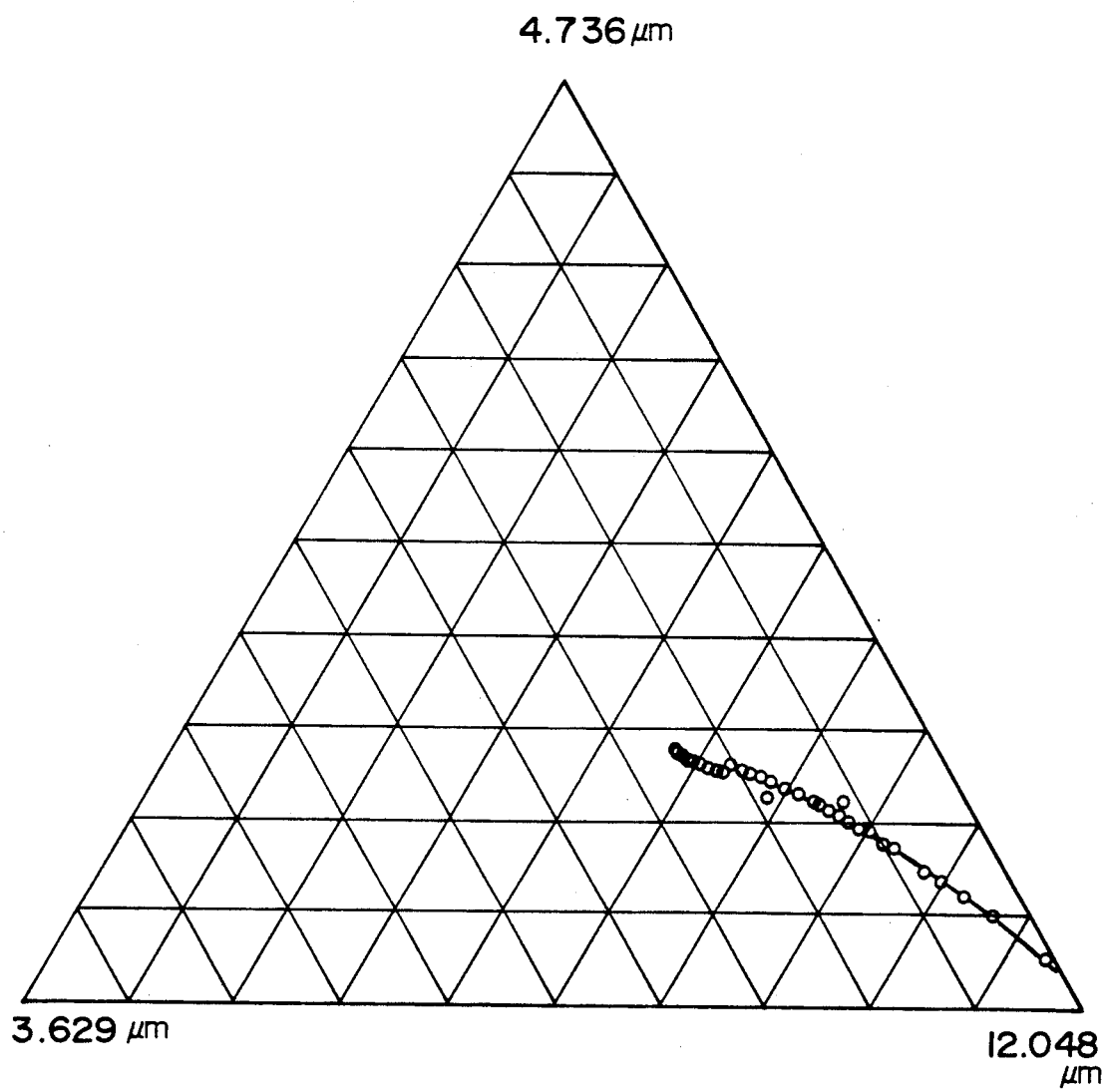
FIG. 14 is a graph representing ratios of the infrared sensors when the experimental apparatus of the second aspect of the present invention monitors a heating panel.

FIG. 14 represents actual ratios of the sensing outputs of the infrared sensors of the experimental apparatus when the heating panel is heated. When the surface temperature of the heating panel was measured with a thermometer during heating of the heating panel, the surface temperature of the heating panel increases at a constant rate to amount to 400° C. in about 45 min.

The FIG. 13 theoretical ratios agree very well with the actual ratios shown in FIG. 14, which establishes that the constants of the equations (1) to (5) are correct.

Figure 15A:
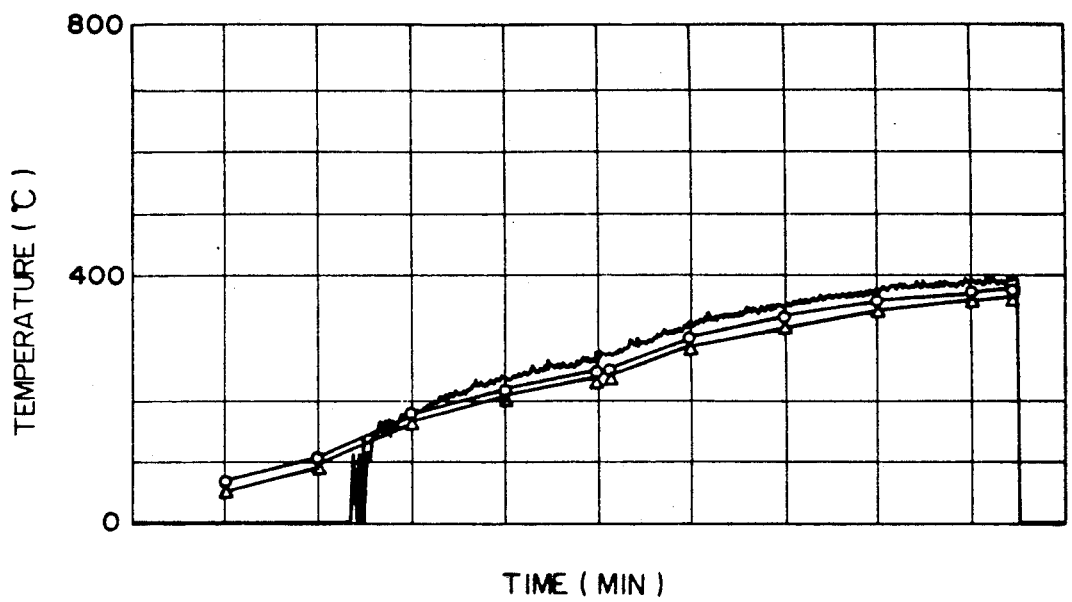
FIG. 15(A) is a graph representing a temperature change computed from the sensing output of the infrared sensors when the experimental apparatus of the present invention monitors the heating panel.

FIG. 15(A) represents a temperature change during heating of the heating panel computed by the equation (3) from outputs of the infrared sensors of the experimental apparatus with the 3.629 $\mu m$ and 12.048 $\mu m$ central sensing wavelengths. In FIG. 15(A), the symbol of a circle represents a maximum of temperature readings of a plurality of thermometers and the symbol of a triangle represents an average of the temperature readings. As seen in FIG. 15(A), the equation (3) is correct for the range of 100° C. or more.

Figure 15B:
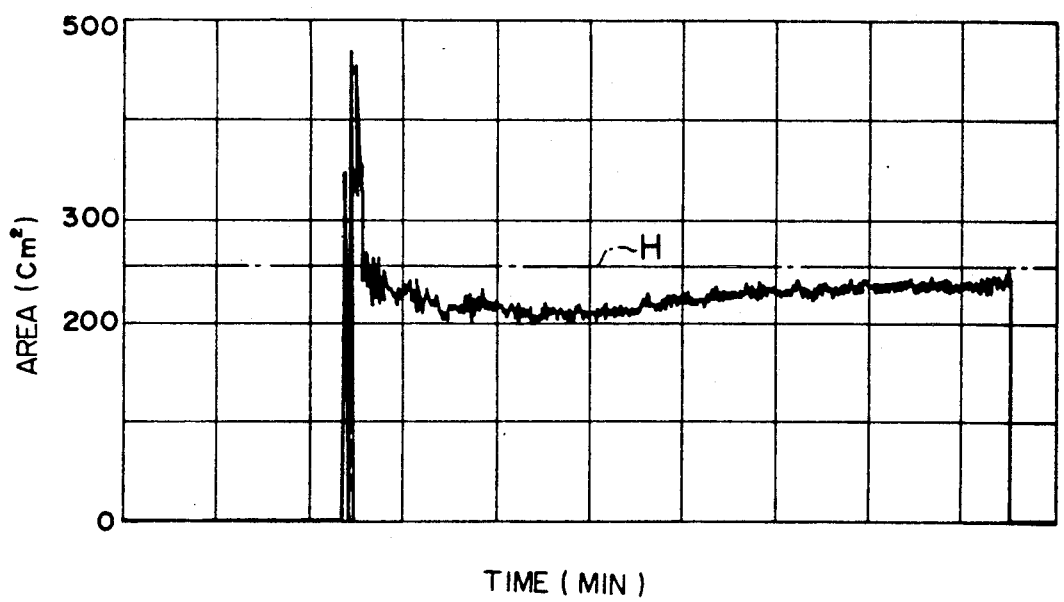
FIG. 15(B) is a graph representing a change in heating area computed from the sensing output of the infrared sensors when the experimental apparatus of the present invention monitors the heating panel.

FIG. 15(B) represents a change in the surface area of the heater computed by the equation (5) from outputs of the infrared sensors of the experimental apparatus. In FIG. 15(B), the alternate long and short dashed line H represents the size of the heating panel. As seen in FIG. 15(B), the theoretical surface area of the heater used with the experimental apparatus computed by the equation (5) agrees well with an actual surface area of the heater beyond the range of about 150° C.

Figure 15C:
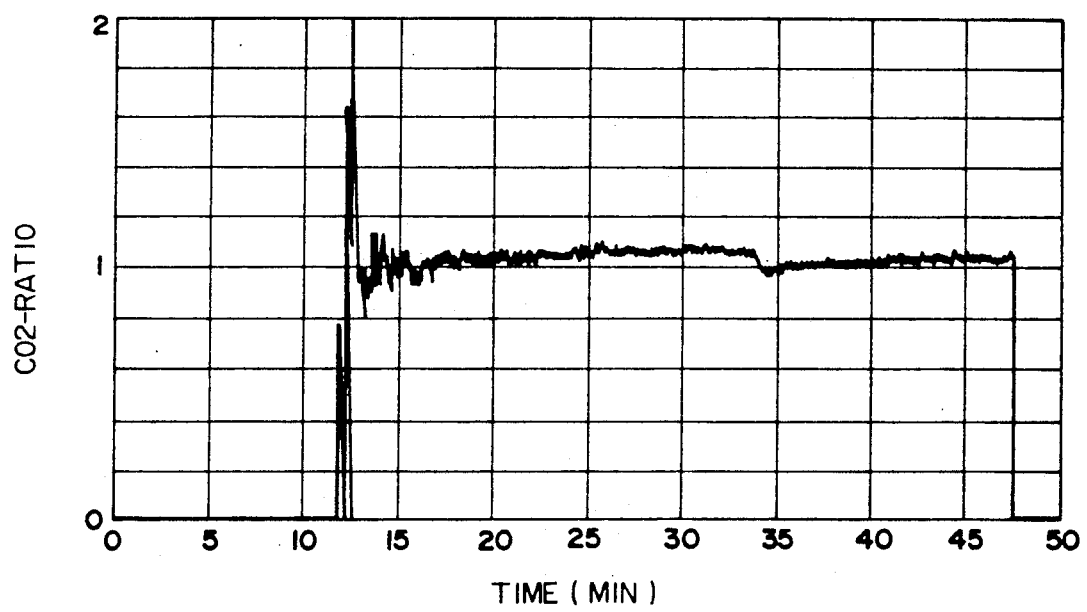
FIG. 15(C) is a graph representing a change in CO2-ratio computed from the sensing output of the infrared sensors when the experimental apparatus of the present invention monitors the heating panel.

FIG. 15(C) represents a ratio (hereinafter referred to as a CO2-ratio.) of theoretical sensing output $V_{CO2}'$ of the infrared sensor estimated from the blackbody radiation intensity $P_{CO2}$ of a $CO_2$-molecular resonance radiation band computed from the outputs of the infrared sensors of the experimental apparatus with sensing wavelengths and an actual sensing output $V_{CO2}$ of a infrared sensor with a 4.736 $\mu m$ central sensing wavelength. In FIG. 15(C), an approximate 1 computed value represents that the infrared sensor with the 4.736 $\mu m$ central wavelength has failed to sense $CO_2$-molecular resonance radiation.

Figure 16A:
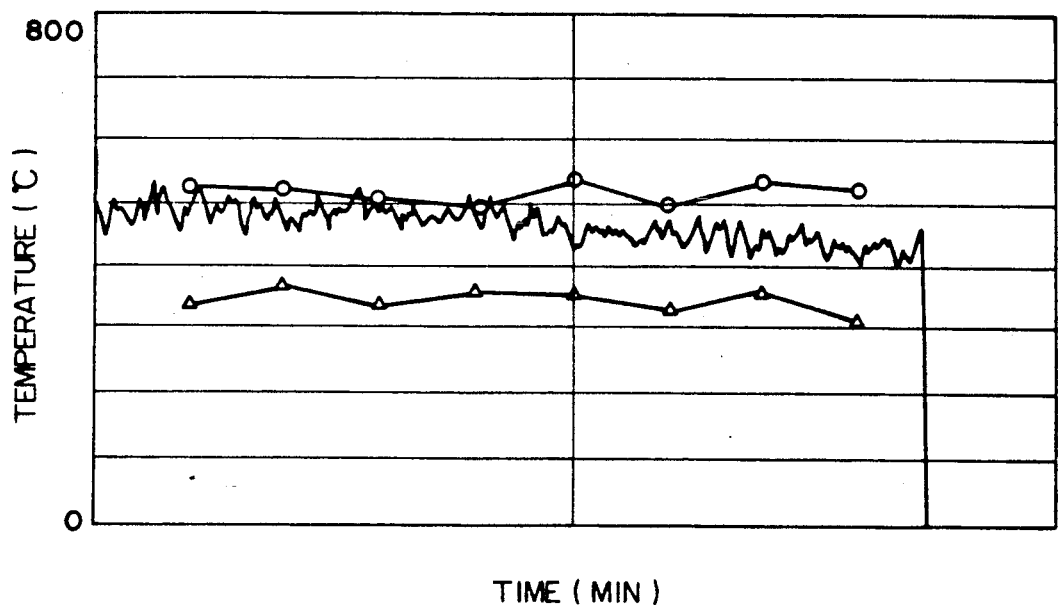
FIG. 16(A) is a graph representing a temperature change computed from the sensing output of the infrared sensors when the experimental apparatus of the present invention monitors a methanol flame.
Figure 16B:
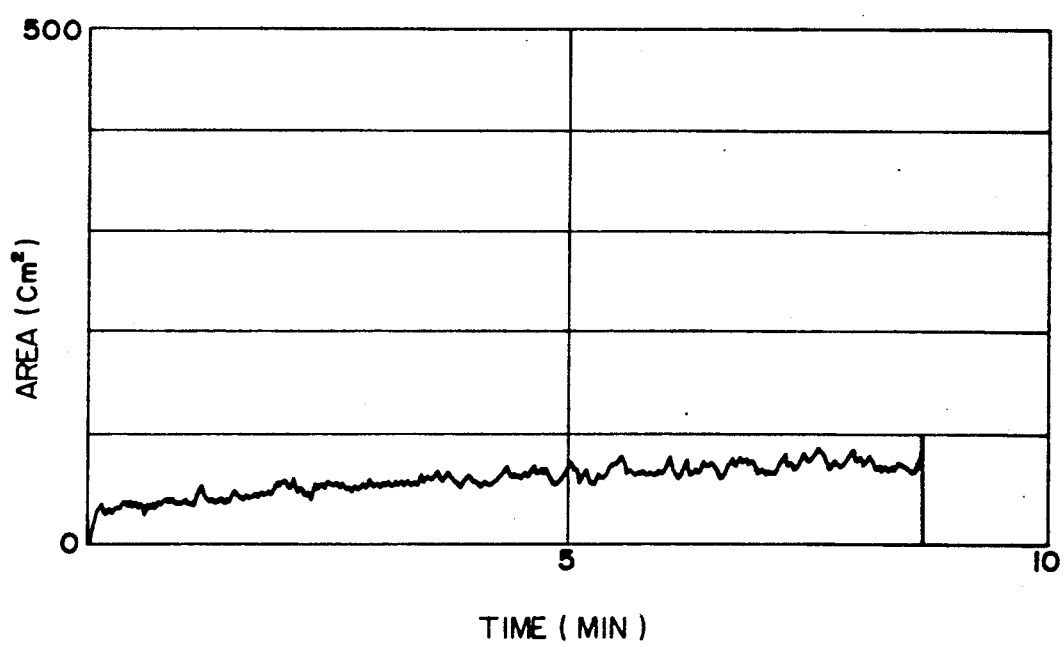
FIG. 16(B) is a graph representing a change in heating area computed from the sensing output of the infrared sensors when the experimental apparatus of the present invention monitors the methanol flame.

FIG. 16(A) represents a change in temperature produced by the experimental apparatus during sensing test of a methanol flame. FIG. 16(B) represents a change in the heating area produced by the experimental apparatus during sensing test of the methanol flame. In the sensing test of the methanol flame, the heating area of the methanol flame was slightly smaller than the opening area (i.e., 10 cm × 10 cm) of the vessel. In this test, the temperature of the overall interior of the vessel was not uniform, but the temperature of a more central part of the interior of the vessel is higher than a more peripheral part of the interior of the vessel. The experimental apparatus is assumed to produce a surface of the more central part with a higher temperature. Since a CO2-ratio of the experimental apparatus exceeded scale, i.e., 4-5 times a CO2-ratio ratio of blackbody radiation, a representation of the CO2-ratio of the experimental apparatus was eliminated.

Figure 17A:
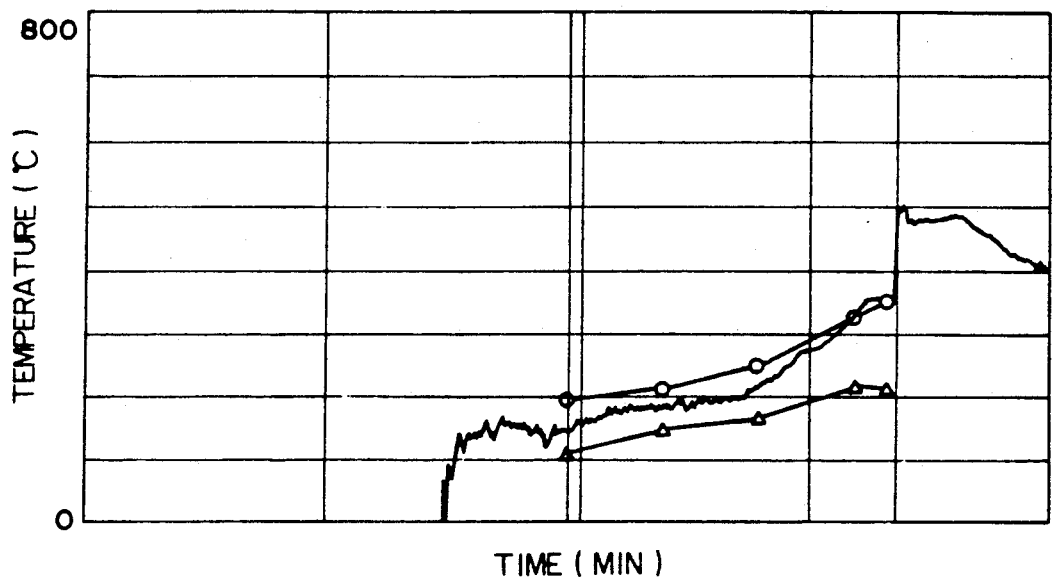
FIG. 17(A) is a graph representing a temperature change computed from the sensing output of the infrared sensors when the experimental apparatus of the present invention monitors a setting fire to a news paper.
Figure 17B:
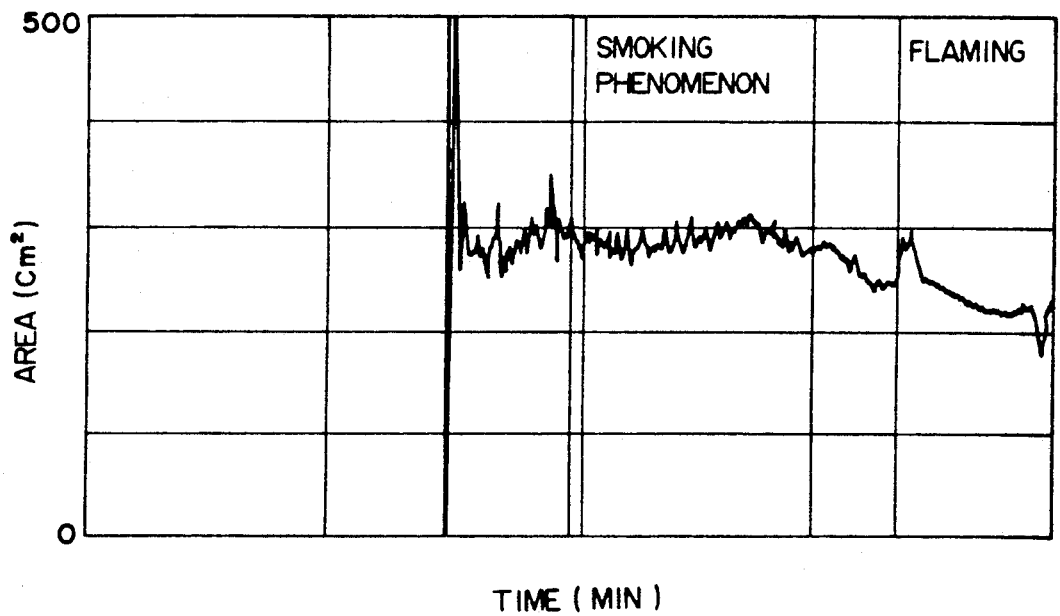
FIG. 17(B) is a graph representing a change computed from the sensing output of the infrared sensors when the experimental apparatus of the present invention monitors the setting fire to the news paper.
Figure 17C:
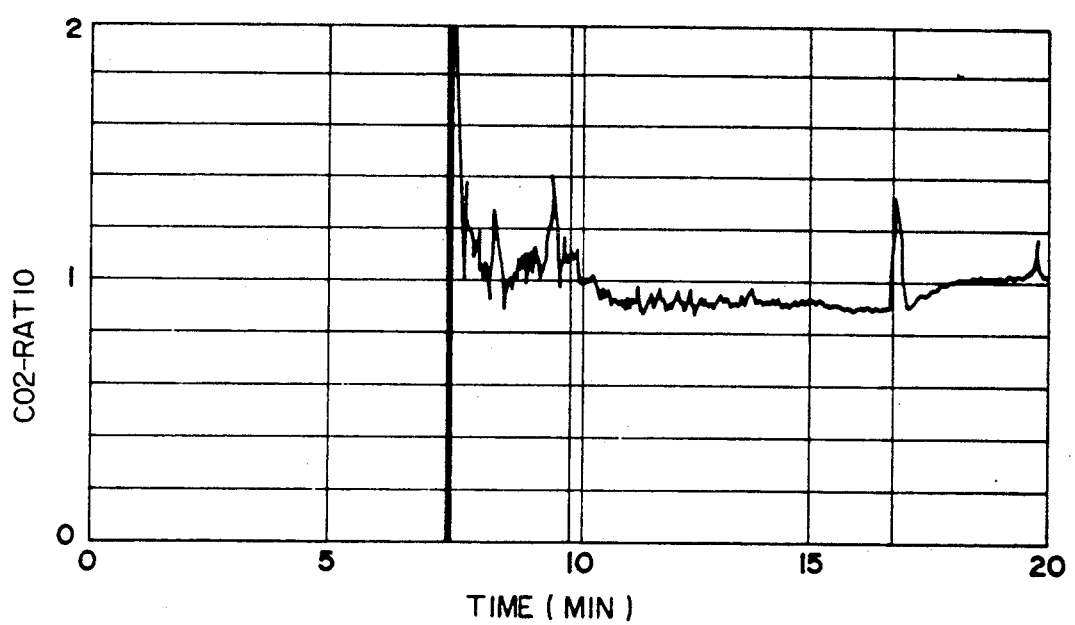
FIG. 17(C) is a graph representing a change in $CO_2$-ratio computed from the sensing output of the infrared sensors when the experimental apparatus of the present invention monitors the setting fire to the news paper.

FIG. 17(A) represents a time change in temperature produced by the experimental apparatus during a firing test for the news papers. FIG. 17(B) represents a time change in the heating area produced by the experimental apparatus during the firing test for the news papers. FIG. 17(C) represents a change in the CO2-ratio produced by the experimental apparatus during the firing test for the news papers.

In the firing test for the news papers, the news papers began to smoke in about 10 min. after the beginning of an operation of the heating panel and then flamed in about 17 min. after said beginning. After flaming, the news papers burned out in a few 10 min.

As seen in FIGS. 17(A) to 17(C), a point of time when a smoking phenomenon of the news papers transferred to a flaming phenomenon thereof, the temperature, heating area and CO2-ration of the heater sharply rose, which agrees well with an actual disastrous fire. After the point of time at 20 min. after the beginning of the news paper firing test, the temperature, heating area and CO2-ratio of the heater essentially became constant in essentially the same manner as in the heating panel heating test, which represents that the underlying heating panel became apparent after the news papers burned out.

As apparent from the test results, the method of the second embodiment of the present invention provides accurate measurements of the temperature and heating area of the heater, provided a noise caused when the temperature of the heater is low must be cared. Thus, this method provides a real-time recognition of a progression of a spreading of a heating area during a spread of disastrous fire and displays or alarms a situation of an increase in the heating area on a monitor or the like placed in a watchman room.

THIRD EMBODIMENT

Figure 18:
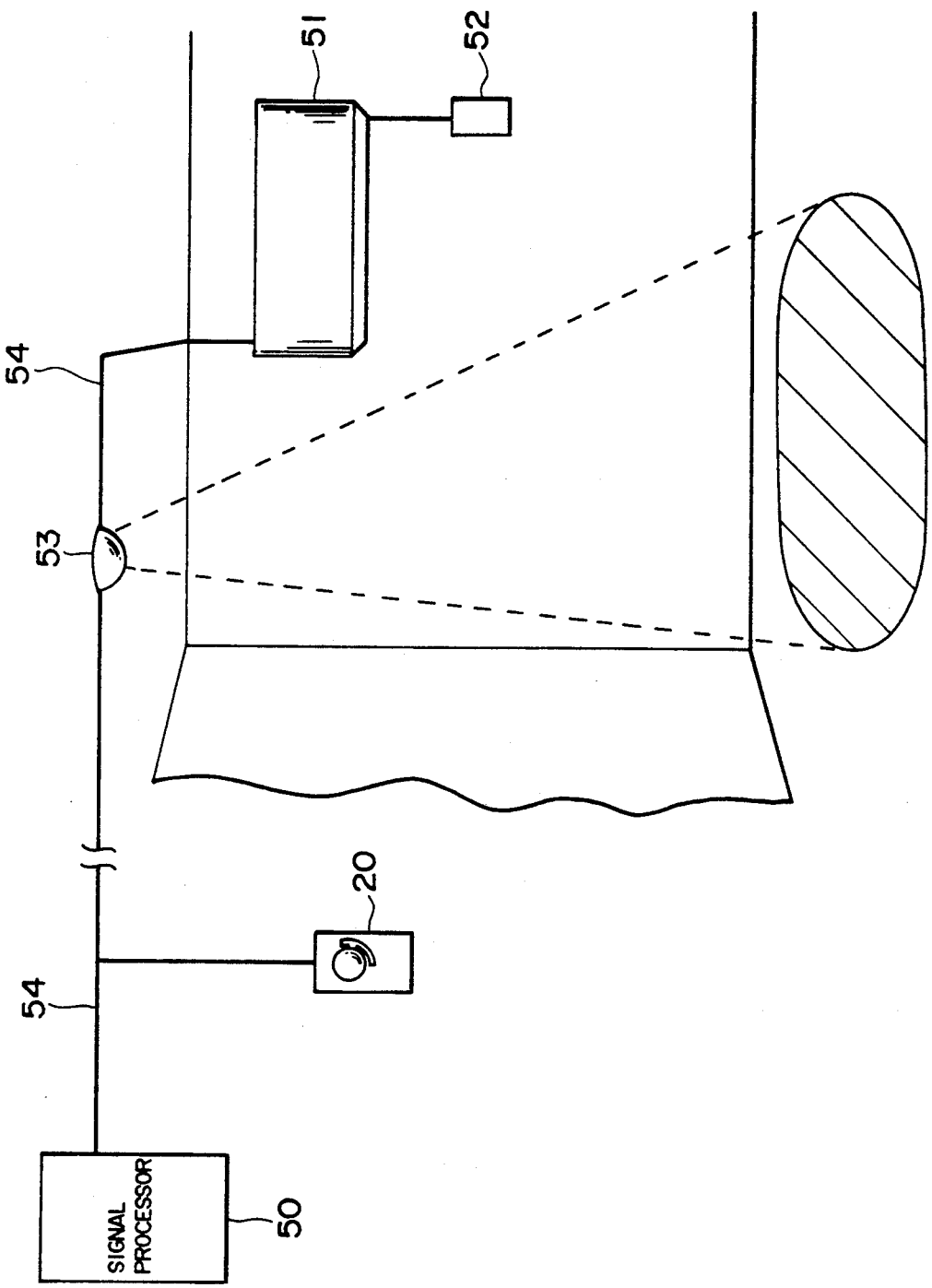
FIG. 18 is a schematic diagram of the fundamental arrangement of one embodiment of an environment monitor of a third aspect of the present invention.

FIG. 18 illustrates the fundamental arrangement of one example of an environment control system embodying an environment monitor of the third aspect of the present invention.

In the third embodiment, an upper portion of an inner wall of a room has an air conditioner 51 attached thereto and the inner wall of the room has a temperature sensor 52 such as a thermistor attached thereto under the air conditioner 51.

The center of the ceiling of the monitored room has an infrared radiation sensing unit 53 attached thereto with a pyroelectric infrared sensor facing downwards. The infrared radiation sensing unit 53, air conditioner 51 and temperature sensor 52 are connected through a cable 54 to a signal processor 50, such as a microcomputer, placed in a watchman room or the like. The signal processor 50 computes a radiation temperature in the monitored room from the outputs of infrared radiation sensing unit 53 and transmits the resulting radiation temperature data to the air conditioner 51. The microcomputer of the air conditioner suitably controls the temperature and flow of a ventilation in response to the radiation temperature data and sensing signal from the temperature sensor 52 in order to produce a comfortable indoor environment.

The signal processor 50 determines the occurence of a disastrous fire in response to the outputs of the infrared radiation sensing unit 53 in order to signal to operate an alarm 20 placed in a watchman room, a passageway etc.

The signal processor 50 monitoring the overall building may alternatively produce a signal controlling the air conditioner 51 in response to the outputs of the temperature sensor 52 and infrared sensor 53 instead of that the air conditioner 51 includes a microcomputer.

The infrared radiation sensing system of the FIG. 1 first embodiment may provide the infrared radiation sensing unit 53 of the environment control system of the third embodiment as it is. That is, the infrared radiation sensing unit 53 comprises a rotational chopper 1 periodically chopping an infrared radiation, infrared filters 2a to 2d and infrared sensors 3a to 3d. The signal processor 50 receiving the sensing outputs of the infrared radiation sensing unit 53 is arranged as shown in FIG. 5 or FIG. 11.

The microcomputer 18 operates on the sensing signals at intervals of a few seconds by timer interruption, stores data of an increase in the temperature of the infrared source and an increase in a heating area and of the presence or absence of $CO_2$-molecular resonance radiation in a few minutes monitors on the data whether the temperature and heating area of the infrared source continuously increase or not, determines an occurrence of a disastrous fire when the temperature and heating area of the infrared source are increasing, and operate a driver 19 to turn a relay RLY on thereby to operate an alarm 20.

In particular, the outputs of the infrared sensors $3a$ to $3d$ change in the case of a disastrous smoking fire as shown in FIG. 6. That is, the outputs a, b, c and d of the infrared sensors $3a$ to $3d$ increase with a temperature increase and an increase in a fire-spreading area in the sequence of the outputs d, c, b and a. Since $CO_2$-molecular resonance radiation sharply rises at the flaming point of time TF, the output c of the infrared sensor $3c$ of the outputs of the infrared sensors $3a$ to $3d$ sharply rises. Then, since the infrared source flames after the flaming point of time TF, the temperature increase is low and an increase in the amount of infrared radiation caused by an increase in the fire spreading area becomes main, so that the outputs a, b, c and d of the infrared sensors $3a$ to $3d$ increase but the ratios of the outputs a, b, c and d essentially becomes constant.

On the other hand, in the case of a nondisastrous fire, the temperature or heating area of the infrared source becomes constant or the condition of an extinguished fire in a fixed time. For example, the heating area of a room heater and a cooking heater will not increase and the temperature thereof becomes constant in a fixed time.

Thus, comparing the outputs of the infrared sensors $3a$ to $3d$ provides a temperature of the infrared source and in particular comparing, e.g., the outputs of the infrared sensors $3a$, $3b$ and $3d$ of the infrared sensors $3a$ to $3d$ at the temperature of the infrared source with predetermined values provides a heating area. In addition, computing from the temperature and heating area of the infrared source produced in the above sequence of operation a blackbody radiation intensity of the infrared source, i.e., an infrared radiation intensity of the $CO_2$-molecular resonance radiation wavelength band if the infrared source is a blackbody and comparing the resulting value of the blackbody radiation intensity with the output of the infrared sensor 3c sensing a $CO_2$-molecular resonance radiation band provide the presence or absence of $CO_2$-molecular resonance radiation.

Thus, when the temperature and heating area of the infrared source tend to increase for a fixed period (i.e., a few minutes) but no $CO_2$-molecular resonance radiation is recognized, the occurence of a disastrous smoking fire is determined. When, the temperature and heating area of the infrared source sharply rise at a point of time and $CO_2$-molecular resonance radiation is concurrently recognized, the microcomputer 18 determines that the disastrous smoking fire has transferred to a disastrous flaming fire and increases the sound volume of the alarm 20 or change the intensity of a sound of the alarm so as to alarm the transference. When a case in which no infrared radiation is sensed suddenly passes into a case in which $CO_2$-molecular resonance radiation is sensed, a heating at a high temperature corresponding to $CO_2$-molecular resonance radiation is sensed and the heating area sharply rises, the microcomputer 18 determines the case as an occurrence of incendiary fire. On the other hand, when no increase in a heating area is recognized, the microcomputer 18 determines the case as a presence of a flaming heater, e.g., a flaming stove.

Thus, the present invention determines whether the presence or absence of disastrous fire on the basis of a very actual fire phenomenon thereby to remarkably reduce the number of occurences of a false alarm as compared to the prior art. During a fire determination routine, a radiation temperature is computed and the resulting temperature data are fed to the air conditioner 51 in order to provide a comfortable indoor environment.

What is claimed is:

1. A fire sensing system, comprising:
    a plurality of band-pass filters separating infrared radiation from a source of infrared radiation into a plurality of wavelength bands;
    an infrared sensor sensing an infrared radiation which has passed through each of said band-pass filters, one of the wavelength bands comprising a $CO_2$-molecular resonance radiation wavelength band;
    a signal processor determining whether a disastrous fire occurs or not in response to outputs of the infrared sensors and a change in a ratio of the outputs of the infrared sensors; and
    a chopper periodically chopping said infrared radiation from said source of infrared radiation in order to provide said infrared radiation to said infrared sensors.

2. A fire sensing system as recited in claim 1, further comprising an infrared sensor for a band of 1-16 μm wavelength.

3. A fire sensing system as recited in claim 1, wherein the pass band of each of said band-pass filters excludes a 5-8 μm wavelength band of infrared radiation.

4. A fire sensing system as recited in claim 1, wherein said signal processor detects the outputs of said infrared sensors synchronous with two periodical signals which are synchronous with the rotation of said chopper, said periodical signals having two 90-degree different phases and said signal processor then produces a mean square of the resulting synchronization-detected signals.

5. A fire sensing system, comprising:
    a plurality of band-pass filters separating infrared radiation from a source of infrared radiation into a plurality of wavelength bands;
    an infrared sensor sensing an infrared radiation which has passed through each of said band-pass filters, one of the wavelength bands comprising a $CO_2$-molecular resonance radiation wavelength band;
    a signal processor determining whether a disastrous fire occurs or not in response to outputs of the infrared sensors and a change in a ratio of the outputs of the infrared sensors, and
    wherein said signal processor computes the blackbody radiation intensity of the sensing band of one of said infrared sensors which senses a $CO_2$-molecular resonance radiation band in response to said one of said infrared sensors, and said signal processor compares the computer blackbody radiation intensity with an output of said one of said infrared sensors in order to sense $CO_2$-molecular resonance radiation and determines an occurrence of a disastrous fire when sensing the $CO_2$-molecular resonance radiation.

6. A fire sensing system as recited in claim 5, wherein said signal processor comprises a filter passing a signal of a predetermined frequency of the sensing outputs of said infrared sensors, a comparator comparing said signal with a predetermined reference level, and a microcomputer determining the existence of an uncontrolled fire in response to a signal produced by the comparator.

7. A process for sensing a fire, comprising the steps of:
    computing the temperature of an infrared source from a ratio of outputs of a plurality of infrared sensors sensing at least two wavelength bands of an infrared radiation from a monitored area;
    computing the intensity of infrared radiation of one of the wavelength bands from said computed temperature;
    computing a heating area from the intensity of the infrared radiation and an output of an infrared sensor sensing said one of the wavelength bands;
    utilizing one of the infrared sensors for sensing a $CO_2$-molecular resonance radiation wavelength band;
    computing the blackbody radiation intensity of the infrared source in a $CO_2$-molecular resonance radiation wavelength band from the temperature and the heating area of the infrared source both computed from an output of the other infrared sensor in accordance with said temperature and heating area computing steps; and
    comparing the computed blackbody radiation intensity with an output of said one of said infrared sensors sensing $CO_2$-molecular resonance radiation and determining an occurrence of a disastrous fire when sensing the $CO_2$-molecular resonance radiation.

8. A process for sensing, a fire as recited in claim 7, wherein a selection determining which of the outputs of said infrared sensors are computed depends on a sensed target temperature.

9. A process for sensing a fire as recited in claim 7, further comprising the step of driving an alarm when determining an occurrence of disastrous fire.

10. A process for sensing a fire as recited in claim 7, further comprising the step of displaying a computed heating area of the infrared source on a monitor.

11. An environment monitor, comprising:
   a plurality of band-pass filters separating infrared radiation from a monitored space into a plurality of wavelength bands;
   an infrared sensor sensing infrared radiation passing through each of said band-pass filters, one of the wavelength bands comprising a $CO_2$-molecular resonance radiation wavelength band;
   a signal processor determining the occurrence of fire and computing a temperature of the infrared radiation from the monitored space from outputs of the infrared sensors of the wavelength bands and a change in a ratio of said sensing outputs; and
   a chopper periodically chopping the infrared radiation from the infrared source in order to provide the infrared radiation to said infrared sensors.

12. An environment monitor as recited in claim 11, further comprising an infrared sensor for a 1-16 $\mu$m wavelength band of infrared radiation.

13. An environment monitor as recited in claim 11, further comprising a contact type temperature sensor for measuring an indoor air temperature and wherein said signal processor produces a signal controlling an air conditioner in response to outputs of said contact type temperature sensor and said infrared sensors.

14. An environment monitor as recited in claim 11, further comprising a contact type temperature sensor for measuring an indoor air temperature and wherein said signal processor produces a signal controlling a room cooler and a room heater in response to outputs of said temperature sensor and said infrared sensors.

15. An environment monitor as recited in claim 11, wherein the pass band of each of said band-pass filters excludes a 5-8 $\mu$m wavelength band of infrared radiation.

16. A process for sensing a fire, which comprises the steps of:
   computing the temperature of an infrared source from outputs of a plurality of infrared sensors sensing at least two different wavelengths by comparing the ratio of said outputs;
   computing the blackbody radiation intensity of at least one of said different wavelengths from said computed temperature;
   computing a heating area of said infrared source from said blackbody radiation intensity and output from said infrared sensor sensing said at least one of said different wavelengths; and
   determining the existence of a uncontrolled fire from changes in said computed temperature and said computed heating area.

17. a process for sensing a fire as recited in claim 16, further comprising the steps of:
   utilizing one of said plurality of infrared sensors for sensing radiation at a wavelength corresponding to $CO_2$-molecular resonance;
   computing the blackbody radiation intensity of said wavelength corresponding to $CO_2$-molecular resonance from said computed temperature and said computed heating area; and
   comparing computed blackbody radiation intensity of said wavelength corresponding to $CO_2$-molecular resonance with an output of said infrared sensor sensing radiation at a wavelength corresponding to $CO_2$-molecular resonance to determine the existence of a flaming infrared source.

18. A process for sensing a fire as recited in claim 16, further comprising the step of displaying said heating area on a display monitor.

19. A fire sensing system, comprising:
   a plurality of band-pass filters separating infrared radiation from a source of infrared radiation into a plurality of wavelength bands, wherein one of said band-pass filters passes a $CO_2$-molecular resonance radiation wavelength band;
   a plurality of infrared sensors sensing said separated infrared radiation which has passed through each of said band-pass filters;
   a signal processor for determining a temperature and a heating area of said source of infrared radiation and determining the existence of an uncontrolled fire based on changes in said temperature and said heating area; and
   a signal processor for determining the existence of a flame in said source of infrared radiation by comparing an output of a sensor sensing said $CO_2$-molecular resonance radiation wavelength with a value predicted by said temperature and said heating area for determining the existence of an uncontrolled flaming fire.

20. A fire sensing system, comprising:
   a plurality of band-pass filters separating infrared radiation from a source of infrared radiation into a plurality of wavelength bands;
   a plurality of infrared sensors sensing said separated infrared radiation which has passed through each of said band-pass filters;
   a signal processor for determining a temperature and a heating area of said source of infrared radiation and determining the existence of an uncontrolled fire based on changes in said temperature and said heating area; and
   a chopper periodically chopping said infrared radiation from said source of infrared radiation in order to provide said infrared radiation to said infrared sensors.

* * * * *